US008648059B2

(12) United States Patent  
Villarreal et al.

(10) Patent No.: US 8,648,059 B2
(45) Date of Patent: Feb. 11, 2014

(54) USE OF EPICATECHIN AND DERIVATIVES AND SALTS THEREOF FOR CARDIAC PROTECTION OF ISCHEMIC MYOCARDIUM AND TO AMELIORATE ADVERSE CARDIAC REMODELING

(75) Inventors: Francisco Villarreal, Chula Vista, CA (US); Katrina Go Yamazaki, La Jolla, CA (US); Pam Rajendran Taub, San Diego, CA (US); Alan Maisel, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 452 days.

(21) Appl. No.: 12/922,170

(22) PCT Filed: Mar. 12, 2009

(86) PCT No.: PCT/US2009/036996
§ 371 (c)(1),
(2), (4) Date: Oct. 15, 2010

(87) PCT Pub. No.: WO2009/114716
PCT Pub. Date: Sep. 17, 2009

(65) Prior Publication Data
US 2011/0021466 A1    Jan. 27, 2011

Related U.S. Application Data

(60) Provisional application No. 61/036,457, filed on Mar. 13, 2008, provisional application No. 61/036,808, filed on Mar. 14, 2008, provisional application No. 61/108,602, filed on Oct. 27, 2008.

(51) Int. Cl.
*A61K 31/65* (2006.01)
(52) U.S. Cl.
USPC .......................................... 514/152; 514/154

(58) Field of Classification Search
USPC .................................................. 514/152, 154
See application file for complete search history.

(56) References Cited

U.S. PATENT DOCUMENTS

| 5,061,703 A * | 10/1991 | Bormann et al. ........ 514/212.01 |
| 2002/0146424 A1 | 10/2002 | Benza et al. |
| 2003/0022847 A1 * | 1/2003 | Lee et al. ........................ 514/39 |
| 2004/0076692 A1 * | 4/2004 | Van Norren et al. .......... 424/730 |
| 2006/0293259 A1 | 12/2006 | Kwik-Uribe et al. |
| 2007/0167419 A1 | 7/2007 | Lapchak et al. |
| 2008/0015169 A1 | 1/2008 | Nelson et al. |

OTHER PUBLICATIONS

Zhou et al., J Nat Prod., 2004;67(12):2063-2069.*
Young, Lee W., International Search Report and Written Opinion, PCT/US09/36996, United States Patent & Trademark Office, Jan. 13, 2010.

* cited by examiner

*Primary Examiner* — San-Ming Hui
(74) *Attorney, Agent, or Firm* — Joseph R. Baker, Jr.; Gavrilovich, Dodd & Lindsey LLP

(57) ABSTRACT

The disclosure provides a method of reducing infarct size in the heart following permanent ischemia or ischemia/reperfusion (IR) event or method for delaying, attenuating or preventing adverse cardiac remodeling comprising administering a drug selected from the group consisting of epicatechin, derivatives thereof and pharmaceutically acceptable salts thereof, wherein the subject is a human or a veterinary animal. Additionally the disclosure provides a method of treating subarachnoid hemorrhage or atrial fibrillation or of enhancing or preserving migration, seeding, proliferation, differentiation and/or survival of stem cells in injured heart tissue comprising administering a drug selected from the group consisting of epicatechin, derivatives thereof and pharmaceutically acceptable salts thereof. The effects of epicatechin administration are sustained over time.

13 Claims, 15 Drawing Sheets

INFARCT SIZE
48 HOURS
AFTER
PERMANENT
CORONARY
OCCLUSION

INFARCT SIZE 3 WEEKS AFTER PERMANENT CORONARY OCCLUSION

Infarct size 48 h after IR: TTC stained sections

CONTROL

DOXYCYCLINE

EPICATECHIN

DOX + EPI

Infarct size 48 h after IR and single dose epicatechin Tx: TTC stained sections

CONTROL 1 mg IV 10 mg IV 50 mg IV

Average reduction in infarct size 48 h after IR after single dose IV epicatechin

USE OF EPICATECHIN AND DERIVATIVES AND SALTS THEREOF FOR CARDIAC PROTECTION OF ISCHEMIC MYOCARDIUM AND TO AMELIORATE ADVERSE CARDIAC REMODELING

CROSS REFERENCE TO RELATED APPLICATIONS

This application is a National Stage Application filed under 35 U.S.C. §371 and claims priority to International Application No. PCT/US09/36996, filed on Mar. 12, 2009, which application claims priority under 35 U.S.C. §119 from Provisional Application Ser. Nos. 61/108,602, filed Oct. 27, 2008, 61/036,457, filed Mar. 13, 2008, and 61/036,868, filed Mar. 14, 2008, all of which are incorporated herein by reference in their entirety.

STATEMENT AS TO FEDERALLY SPONSORED RESEARCH

This invention was made with Government support under Grant Nos. HL043617 and HL067922 awarded by the National Institutes of Health. The Government has certain rights in the invention.

BACKGROUND

The following discussion of the background of the invention is merely provided to aid the reader in understanding the disclosure and is not admitted to describe or constitute prior art.

Ischemic organ injury, and the related condition of ischemia/reperfusion injury, is accompanied by changes in signaling molecules and metabolic effectors that can, independently or in concert, trigger cell death in its various forms. These include changes in intracellular pH, calcium, ceramide, free radicals, hypoxia and adenosine triphosphate (ATP) depletion. While all of these factors may be significantly altered as a consequence of acute necrotic cell death, they can also be specific effectors of apoptotic death under certain circumstances.

The contributions of apoptotic cell death and cellular necrosis to functional deterioration of the organ in ischemic conditions such as myocardial infarction and stroke are well established. Myocardial infarctions generally result in an immediate depression in ventricular function due to myocardial cell necrosis and apoptosis. These infarctions are also likely to expand, provoking a cascading sequence of myocellular and structural events which ultimately result in adverse cardiac remodeling. In many cases, this progressive myocardial infarct expansion and adverse ventricular remodeling (thinning of left ventricular wall, scar tissue formation) leads to deterioration in ventricular function and heart failure.

Ischemic renal injury has been traditionally associated with tubular cell necrosis along with obstructive cast formation, disruption of architecture, and a significant inflammatory response. More recently apoptosis has emerged as a significant mode of cell death during ischemic renal injury. While the contribution of apoptotic cell death to functional deterioration of the organ is obvious in conditions like myocardial infarction and stroke, it is less clear how apoptotic dropout of tubular cells can impact glomerular filtration rate (GFR). Nevertheless, recent reports have demonstrated that interference with the apoptotic program does translate into a protective effect on renal function.

Despite considerable advances in the diagnosis and treatment of conditions related to apoptosis and cellular necrosis, there remains a need in the art for prophylactic and therapeutic approaches for the treatment of these conditions.

SUMMARY

The disclosure relates generally to methods and compositions for the prophylactic and therapeutic treatment of conditions related to apoptosis and cellular necrosis, including ischemia and reperfusion injury, aneurysm, acute coronary syndromes, renal injury, etc.

The disclosure provides compositions and methods for prophylactic and/or therapeutic treatment of diseases related to apoptosis and cellular necrosis. In various aspects described hereinafter, the disclosure provides compositions and methods for treatment of acute coronary syndromes, including but not limited to myocardial infarction; acute ischemic events in other organs and tissues, including but not limited to renal injury, renal ischemia and diseases of the aorta and its branches; and injuries arising from medical interventions including, but not limited to, coronary artery bypass grafting (CABG) procedures and aneurysm repair.

In one embodiment, the disclosure is directed to methods of treating organ or tissue ischemia, and most typically an acute ischemic or ischemia/reperfusion (IR) event in a subject. These methods comprise administering to a subject in need thereof a drug (also referred to herein as a "pharmaceutical composition") selected from the group consisting of epicatechin, derivatives thereof and pharmaceutically acceptable salts thereof. Typically, epicatechin, a derivative thereof or a pharmaceutically acceptable salt thereof is administered together with one or more tetracycline antibiotics such as doxycycline.

In a further embodiment, the subject is selected based on the occurrence of a myocardial infarction. The method is useful to reduce infarct size in the heart of the subject, and/or delays, attenuates or prevents adverse cardiac remodeling in the subject.

In other embodiments, the subject is selected based on the occurrence of a renal injury. In a further embodiment, the method reduces the progression of the renal injury to renal failure.

In other embodiments, the subject is selected based on the occurrence of a total coronary occlusion. In a further embodiment, the method reduces infarct size in the heart of the subject, and/or delays, attenuates or prevents adverse cardiac remodeling in the subject.

In yet other embodiments, the subject is selected based on the occurrence of myocardial ischemia (e.g., angina or AMI).

In yet further embodiments, the subject is selected based on the occurrence of a stroke. In one embodiment, the method delays, attenuates or prevents development of cerebral infarction, cell death, brain swelling, and/or cerebral vasospasm.

In other embodiments, the subject is selected based on the occurrence of an aortic aneurysm. In such embodiments, the method delays, attenuates or prevents dissection, rupture, renal injury, and/or enlargement of the aneurysm.

In yet other embodiments, the subject is selected based on the occurrence of atrial fibrillation. In these embodiments, the method delays, attenuates or prevents adverse remodeling of the atrium, resulting in reduced substrate for arrhythmia.

In another embodiment, the subject is selected based on the occurrence of medical intervention causing temporary acute ischemia, including but not limited to CABG surgery, aneurysm repair, angioplasty, administering a radiocontrast agent, etc. In such embodiments, the method delays, attenuates or prevents the occurrence of ischemic organ injury.

While in some embodiments two or more drugs be "administered together" in the same pharmaceutical composition, the phrase as used herein is not intended to imply that this must be so. Rather, two or more pharmaceuticals are "administered together" if the $T_{1/2}$ for the clearances of each pharmaceutical from the body overlap at least partially with one another. For example, if a first pharmaceutical has a $T_{1/2}$ for clearance of 1 hour and is administered at time=0, and a second pharmaceutical has a $T_{1/2}$ for clearance of 1 hour and is administered at time=45 minutes, such pharmaceuticals are considered administered together. Conversely, if the second drug is administered at time=2 hours, such pharmaceuticals are not considered administered together.

Routes of administration for the pharmaceutical compositions of the disclosure include parenteral and enteral routes. Typical enteral routes of administration include delivery by mouth (oral), nasal, rectal, and vaginal routes. Typical parenteral routes of administration include intravenous, intramuscular, subcutaneous, and intraperitoneal routes. When more than one pharmaceutical composition is being administered, each need not be administered by the same route.

As noted above, in certain embodiments, epicatechin, or a derivative or pharmaceutically acceptable salt thereof, is administered together intravenously with one or more tetracycline antibiotics such as doxycycline, typically in a single pharmaceutical composition. In some embodiment, the epicatechin derivative has 3R(−) stereochemistry. Such administration may be followed by further administrations of one or both of these drug compounds. For example, epicatechin and doxycycline may be administered to a subject within 24 hours of the onset of an ischemic or ischemia/reperfusion event; and this may be followed for one or more days in which the subject receives epicatechin or another derivative or pharmaceutically acceptable salt thereof, and/or one or more tetracycline antibiotics at the same or different concentrations and by the same or different delivery routes. In certain embodiments, the initial administration is by an intravenous route, and the subsequent "maintenance" administrations are by an oral route.

Typically, the pharmaceutical compositions of the disclosure are administered in an "effective amount." This term is defined hereinafter. Unless dictated otherwise, explicitly or otherwise, an "effective amount" is not limited to a minimal amount sufficient to ameliorate a condition, or to an amount that results in an optimal or a maximal amelioration of the condition. In the case when two or more pharmaceuticals are administered together, an effective amount of one such pharmaceutical may not be, in and of itself, be an effective amount, but may be an effective amount when used together with additional pharmaceuticals.

In certain embodiments, the pharmaceutical compositions of the disclosure are administered within 48 hours of the onset of an ischemic or ischemia/reperfusion event, within 48 hours of initiating a medical procedure, or within 48 hours of presentation for medical treatment. Onset of an event may be identified by self-reporting of the subject, by knowing the time of initiation of a medical procedure, or by some objective measure of an event occurrence.

In some embodiments, the pharmaceutical compositions of the disclosure are administered within 24 hours of the onset of an ischemic or ischemia/reperfusion event, initiating a medical procedure or patient presentation, typically within 12 hours, and more typically within 6 hours. A pharmaceutical composition is administered "within x hours" of an event, medical procedure, or patient presentation is it is administered between x hours before or after the event, medical procedure, or patient presentation.

In the case of an ischemic event involving the heart, typical objective measures include increases in one or more cardiac markers (e.g., CK-MB, myoglobin, cardiac troponin I, cardiac troponin T, B-type Natriuretic peptide, NT-proBNP, etc.); changes in serial ECG tracings, MRI studies, and/or nuclear imaging results; and angiographic results.

In the case of an ischemic event involving the kidneys, typical objective measures include those described by Bellomo et al., Crit Care. 8(4):R204-12, 2004, which is hereby incorporated by reference in its entirety. This reference proposes the following classifications for stratifying acute kidney injury patients: "Risk": serum creatinine increased 1.5 fold from baseline OR urine production of <0.5 ml/kg body weight for 6 hours; "Injury": serum creatinine increased 2.0 fold from baseline OR urine production<0.5 ml/kg for 12 h; "Failure": serum creatinine increased 3.0 fold from baseline OR creatinine>355 μmol/l (with a rise of >44) or urine output below 0.3 ml/kg for 24 h.

In a related aspect, the disclosure is directed to pharmaceutical compositions for treatment of an acute ischemic or ischemia/reperfusion (IR) event. This composition comprises an effective amount of epicatechin, or a derivative or pharmaceutically acceptable salt thereof, and one or more additional drugs useful in the treatment of ischemic or ischemia/reperfusion events. In particularly embodiments, the pharmaceutical composition comprises epicatechin, or a derivative or pharmaceutically acceptable salt thereof, and one or more tetracycline antibiotics, most typically doxycycline. Typically, the composition is formulated for intravenous delivery.

In another aspect, the disclosure is directed to a method of enhancing or preserving migration, seeding, proliferation, differentiation and/or survival of stem cells in injured heart tissue of a subject comprising administering to a subject in need thereof a drug selected from the group consisting of epicatechin, derivatives thereof and pharmaceutically acceptable salts thereof.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
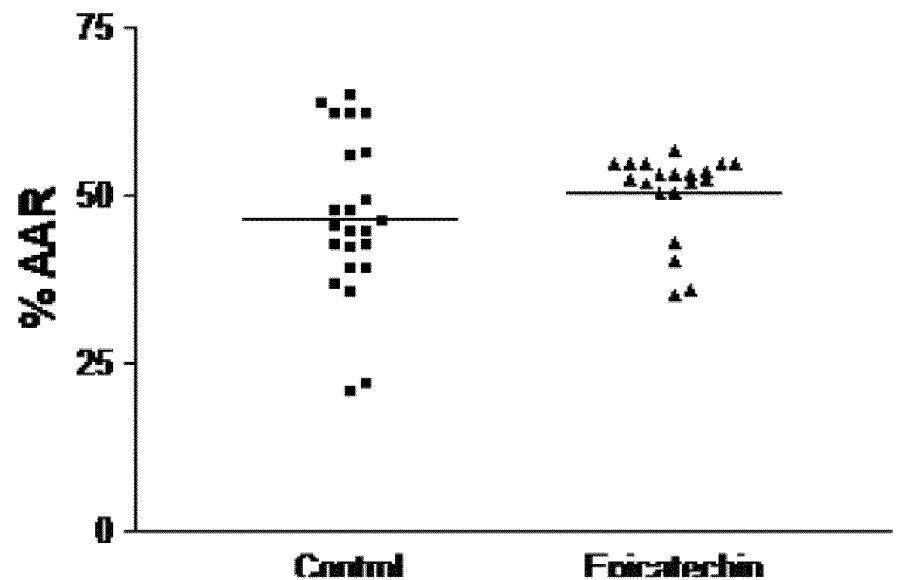
FIG. 1 is a dispersion plot for all individual data points recorded on measurements of area at risk (AAR) and infarct size (derived as a function of AAR) in animals subjected to IR injury and either control (i.e. vehicle) or epicatechin treatment in the temporary occlusion experiment. As demonstrated by the results AAR was similar both in untreated and treated animals indicating that epicatechin treatment does not alter the coronary vasculature. As can be observed animals subjected to epicatechin treatment demonstrated an approximate 50% reduction in infarct size.
Figure 1:
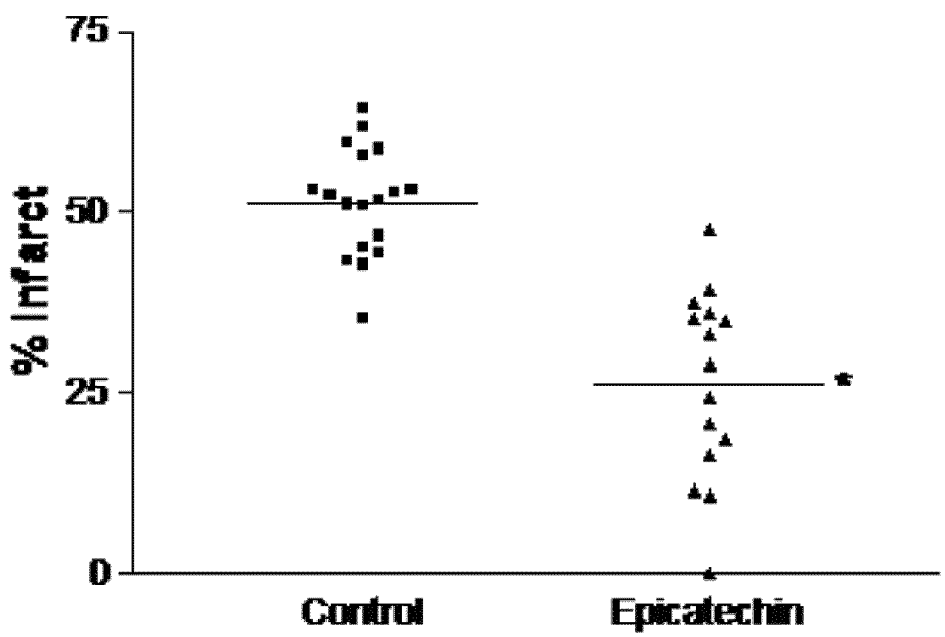

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the disclosure. Nothing herein is to be construed as an admission that the inventors are not entitled to antedate such disclosure by virtue of prior disclosure.

Ischemia and reperfusion are physiologically different events and do not necessarily occur at the same time. As ischemia refers to deficiency of blood to a part typically due to a thrombus or embolus and reperfusion injury results when the obstruction or constriction is removed, it is possible and desirable to reduce the potential infarct size and adverse remodeling during the ischemia/reperfusion event. The disclosure demonstrates that epicatechin or a derivative thereof either alone or in combination with a tetracycline or derivative thereof inhibit ischemic and/or reperfusion injury. The disclosure provides methods and compositions useful for inhibiting ischemic and/or reperfusion injury comprising, for example, administering a epicatechin during the ischemia or alternatively after the ischemia, but before reperfusion has occurred, or alternatively after the ischemia and at the time of reperfusion. Disclosed herein are methods wherein epicatechin, a derivative thereof or a pharmaceutically acceptable salt thereof is administered during, prior to, or after an ischemia/reperfusion event.

Tissues deprived of blood and oxygen suffer ischemic necrosis or infarction, often resulting in permanent tissue damage. Cardiac ischemia is often termed "angina", "heart disease", or a "heart attack", and cerebral ischemia is often termed a "stroke". Both cardiac and cerebral ischemia result from decreased blood and oxygen flow which is often followed by some degree of brain damage, damage to heart tissue, or both. The decrease in blood flow and oxygenation may be the result of occlusion of arteries, rupture of vessels, developmental malformation, altered viscosity or other quality of blood, or physical traumas. Diabetes is a risk factor for ischemia. Accordingly, methods and compositions of the disclosure can be used to prevent or inhibit the risk of ischemia or inhibit and reduce the damage caused by ischemic injury in diabetic patients. This can include ischemia resulting in vision loss and ulcerations in addition to cardiac and cerebral ischemic injury.

Loss of blood flow to a particular vascular region is known as focal ischemia; loss of blood flow to the entire brain, global ischemia. When deprived of blood, and thus, oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Spinal cord injury is the most serious complication of spinal column trauma and also of operations on the aorta for treatment of thoracic and thoracoabdominal aneurysms (Kouchoukos, J. Thorac. Cardiovasc. Surg. 99:659-664, (1990)). As described in U.S. Pat. No. 5,648,331, the spinal cord is the organ most sensitive to ischemia during cross-clamping of the aorta, where the resultant injury may produce paraparesis or paraplegia. Spinal cord ischemia and paraplegia develop in approximately eleven percent (11%) of patients undergoing elective descending thoracic and thoracoabdominal aneurysm repair and nearly forty percent (40%) undergoing emergent repairs (Crawford, J. Vas. Surg. 3:389-402, (1986)).

Myocardial ischemia occurs when the heart muscle does not receive an adequate blood supply and is thus deprived of necessary levels of oxygen and nutrients. A common cause of myocardial ischemia is atherosclerosis, which causes blockages in the blood vessels (coronary arteries) that provide blood flow to the heart muscle. Congestive heart failure (CHF) can also result from myocardial infarction followed by cardiac remodeling.

Ischemic events affecting the intestines play a major role of the mortality and morbidity or numerous patients. As described in U.S. Pat. No. 6,191,109, ischemic injury to the small intestine leads to mucosol destruction, bacterial translocation and perforation.

Age-related macular degeneration (AMD) is the leading cause of visual impairment and blindness in the United States and elsewhere among people 65 years or older. Oxidative damage to the retina may be involved in the pathogenesis of AMD.

Reactive oxygen species (ROS), also designated free radicals, include among other compounds singlet oxygen, the superoxide anion (O2-), nitric oxide (NO), and hydroxyl radicals. Mitochondria are particularly susceptible to damage included by ROS, as these are generated continuously by the mitochondrial respiratory chain. Production of ROS increases when cells experience a variety of stresses, including organ ischemia and reperfusion, ultraviolet light exposure and other forms of radiation. Reiter et al. (1998) Ann. N.Y. Acad. Sci. 854:410-424; Saini et al. (1998) Res. Comm. Mol. Pathol. Pharmacol. 101:259-268; Gebicki et al. (1.999) Biochem. J. 338:629-636. ROS are also produced in response to cerebral ischemia, including that caused by stroke, traumatic head injury and spinal injury. In addition, when metabolism increases or a body is subjected to extreme exercise, the endogenous antioxidant systems are overwhelmed, and free radical damage can take place. Free radicals are reported to cause the tissue-damage associated with some toxins and unhealthful conditions, including toxin-induced liver injury. Obata (1997) J. Pharm. Pharmacol. 49:724-730; Brent et al. (1992) J. Toxicol. Clin. Toxicol. 31:173-196; Rizzo et al. (1994) Zentralbl. Veterinarmed. 41:81-90; Lecanu et al. (1998) Neuroreport 9:559-663.

The disclosure provides a method for treating and/or ameliorating the symptoms of a tissue ischemic condition in a mammalian subject, comprising administering to the subject an effective amount of an epicatechin or epicatechin derivative alone or in combination with a tetracycline derivative composition, and by said administering, reducing tissue damage related to said tissue ischemic condition. The disclosure also provides a method for treating and/or ameliorating the symptoms of a tissue ischemic condition in a mammalian subject, comprising administering to the subject an effective amount of an epicatechin or epicatechin derivative alone or in combination with a tetracycline derivative, and by said administering, reducing tissue damage related to said tissue ischemic condition. In some embodiments, the tissue ischemic condition is selected from the group consisting of cerebral ischemia; intestinal ischemia; spinal cord ischemia; cardiovascular ischemia; myocardial ischemia associated with myocardial infarction; mycardial ischemia associated with CHF, ischemia associated with age-related macular degeneration (AME); liver ischemia; kidney/renal ischemia; dermal ischemia; vasoconstriction-induced tissue ischemia; penile ischemia as a consequence of priapism and erectile dysfunction; ischemia associated with thromboembolytic disease; ischemia associated with microvascular disease; and ischemia associated with diabetic ulcers, gangrenous conditions, post-trauma syndrome, cardiac arrest resuscitation, hypothermia, peripheral nerve damage or neuropathies. In some embodiments, the tissue ischemic condition is cerebral ischemia. In further embodiments, a composition comprises an epicatechin or epicatechin derivative alone or in combination with a tetracycline derivative is in a range of about 1 to about 1000 mg per kg body weight of said mammalian subject. In additional embodiments, a composition comprises an epicatechin or epicatechin derivative alone or in combination with a tetracycline derivative in a range of about 1 to about 50 mg per kg body weight of said mammalian subject. In yet additional embodiments, a composition comprises an epicatechin or epicatechin derivative alone or in combination with a tetracycline derivative in a range of about 10 to about 100 mg per kg body weight of said mammalian subject.

The disclosure also provides a method for treating and/or ameliorating the symptoms of a tissue ischemic condition in a mammalian subject, comprising administering to the subject an effective amount of an epicatechin or epicatechin derivative alone or in combination with a tetracycline derivative composition, and by said administering, reducing tissue damage related to said tissue ischemic condition. The disclosure also provides a method for treating and/or ameliorating the symptoms of a tissue ischemic condition in a mammalian subject, comprising administering to the subject an effective amount of an epicatechin or epicatechin derivative alone or in combination with a tetracycline derivative composition, and by said administering, reducing tissue damage related to said tissue ischemic condition. In some embodiments, the tissue ischemic condition is selected from the group consisting of cerebral ischemia; intestinal ischemia; spinal cord ischemia; cardiovascular ischemia; myocardial ischemia associated with myocardial infarction; mycardial ischemia associated with CHF, ischemia associated with age-related macular degeneration (AMD); liver ischemia; kidney ischemia; dermal ischemia; vasoconstriction-induced tissue ischemia; penile ischemia as a consequence of priapism; ischemia associated with thromboembolytic disease; ischemia associated with microvascular disease; and ischemia associated with diabetic ulcers, gangrenous conditions, post-trauma syndrome, cardiac arrest resuscitation, peripheral nerve damage or neuropathies. In further embodiments, the tissue ischemic condition is cerebral ischemia. In further embodiments, a composition comprises an epicatechin or epicatechin derivative alone or in combination with a tetracycline derivative in a range of about 1 to about 1000 mg per kg body weight of said mammalian subject. In additional embodiments, a composition comprises an epicatechin or epicatechin derivative alone or in combination with a tetracycline derivative in a range of about 1 to about 50 mg per kg body weight of said mammalian subject. In yet further embodiments, a composition comprises an epicatechin or epicatechin derivative alone or in combination with a tetracycline derivative in a range of about 10 to about 100 mg per kg body weight of said mammalian subject.

The disclosure also provides a method for treating and/or ameliorating the symptoms of a non-cardiovascular tissue ischemic condition in a mammalian subject, comprising administering to the subject an effective amount of an epicatechin or epicatechin derivative alone or in combination with a tetracycline derivative composition, and by said administering, reducing tissue damage related to said non-cardiovascular tissue ischemic condition. The disclosure also provides a method for treating and/or ameliorating the symptoms of a non-cardiovascular tissue ischemic condition in a mammalian subject, comprising administering to the subject an effective amount of an epicatechin or epicatechin derivative alone or in combination with a tetracycline derivative composition, and by said administering, reducing tissue damage related to said non-cardiovascular tissue ischemic condition. In some embodiments, the tissue ischemic condition is selected from the group consisting of intestinal ischemia; spinal cord ischemia; ischemia associated with age-related macular degeneration (AMD); liver ischemia; kidney ischemia; dermal ischemia; vasoconstriction-induced tissue ischemia; penile ischemia as a consequence of priapism; ischemia associated with thromboembolytic disease; ischemia associated with microvascular disease; and ischemia associated with diabetic ulcers, gangrenous conditions, post-trauma syndrome, peripheral nerve damage or neuropathies. In some embodiments, a composition comprises an epicatechin or epicatechin derivative alone or in combination with a tetracycline derivative in a range of about 1 to about 1000 mg per kg body weight of said mammalian subject. In further embodiments, a composition comprises an epicatechin or epicatechin derivative alone or in combination with a tetracycline derivative in a range of about 1 to about 50 mg per kg body weight of said mammalian subject. In yet additional embodiments, a composition comprises an epicatechin or epicatechin derivative alone or in combination with a tetracycline derivative in a range of about 10 to about 100 mg per kg body weight of said mammalian subject.

The disclosure also provides a method for treating and/or ameliorating the symptoms of a tissue ischemic condition in a mammalian subject, comprising administering to the subject an effective amount of a composition comprising a an epicatechin or epicatechin derivative alone or in combination with a tetracycline derivative, and by said administering, reducing tissue damage related to said tissue ischemic condition, wherein said tetracycline derivative is a doxycycline or derivative. In some embodiments, the tissue ischemic condition is selected from the group consisting of intestinal ischemia; spinal cord ischemia; ischemia associated with age-related macular degeneration (AMD); liver ischemia; kidney ischemia; dermal ischemia; vasoconstriction-induced tissue ischemia; penile ischemia as a consequence of priapism; ischemia associated with thromboembolytic disease; ischemia associated with microvascular disease; and ischemia associated with diabetic ulcers, gangrenous conditions, post-trauma syndrome, peripheral nerve damage or neuropathies.

"Tissue Ischemia" or "tissue ischemic" or "a tissue ischemic condition" refer to a medical event which is pathological in origin, or to a surgical intervention which is imposed on a subject, wherein circulation to a region of the tissue is impeded or blocked, either temporarily, as in vasospasm or transient ischemic attach (TIA) in cerebral ischemia or permanently, as in thrombolic occlusion in cerebral ischemia. The affected region is deprived of oxygen and nutrients as a consequence of the ischemic event. This deprivation leads to the injuries of infarction or in the region affected. The disclosure encompasses cerebral ischemia; intestinal ischemia; spinal cord ischemia; cardiovascular ischemia; ischemia associated with CHF, liver ischemia; kidney ischemia; dermal ischemia; vasoconstriction-induced tissue ischemia, such as a consequence of Raynaud's disorder; penile ischemia as a consequence of priapism; and ischemia associated with thromboembolytic disease; microvascular disease; such as for example diabetes and vasculitis; diabetic ulcers; gangrenous conditions; post-trauma syndrome; cardiac arrest resuscitation; and peripheral nerve damage and neuropathies; and other ischemias, including ischemia associated with ocular health concerns, such as for example, age-related macular degeneration (AMD). Ischemia occurs in the brain during, for example, a stroke, cardiac arrest, severe blood loss due to injury or internal hemorrhage and other similar conditions that disrupt normal blood flow. Ischemia occurs in myocardial tissue as a result of, for example, atherosclerosis and CHF. It may also occur after a trauma to the tissue since the pressure caused by edema presses against and flattens the arteries and veins inside the tissue, thereby reducing their ability to carry blood through the tissue. Cerebral ischemia may also occur as a result of macro- or micro-emboli, such as may occur subsequent to cardiopulmonary bypass surgery. Age-related macular degeneration may be associated with oxidative damage to the retina as a result of an ischemic condition. As used herein, a "non-cardiovascular" ischemic condition specifically excludes an ischemic condition of the cardio-pulmonary system or circulatory system. As used herein, a "non-cerebral" ischemic condition specifically excludes an ischemic condition of the brain.

"Cerebral Ischemia" or "cerebral ischemic" or "a cerebral ischemic condition" refer to a medical event which is pathological in origin, or to a surgical intervention which is imposed on a subject, wherein circulation to a region of the brain is impeded or blocked, either temporarily, as in vasospasm or transient ischemic attach (TIA) or permanently, as in thrombolic occlusion. The affected region is deprived of oxygen and nutrients as a consequence of the ischemic event. This deprivation leads to the injuries of infarction or in the region affected. Ischemia occurs in the brain during, for example, a thromboembolic stroke, hemorrhagic stroke, cerebral vasospasm, head trauma, cardiac arrest, severe blood loss due to injury or internal hemorrhage and other similar conditions that disrupt normal blood flow. It may also occur after a head trauma, since the pressure caused by edema presses against and flattens the arteries and veins inside the brain, thereby reducing their ability to carry blood through the brain. Cerebral ischemia may also occur as a result of macro- or micro-emboli, such as may occur subsequent to cardiopulmonary bypass surgery.

In one aspect, methods of the disclosure relate to preventing neuronal damage in a mammalian subject at risk of developing injury due to a cerebral ischemic condition, e.g. for example, by an infarct in the brain. The methods of reducing neuronal damage relate to minimizing the extent and/or severity of injury in the brain associated with or due to a cerebral ischemic condition by ameliorating or reducing the injury that would otherwise occur. The methods encompass administering an epicatechin, epicatechin derivative alone or in combination with a tetracycline derivative to a subject. The amount administered and the duration of the treatment are effective to minimize the size and/or severity of the neuronal damage in the mammalian subject as measured by for example, reduction in neuronal cell death and/or reduction in cerebral edema associated with a cerebral ischemic condition and/or reduction in cognitive disorder and/or reduction in infarct size. Thus, it is anticipated that as a result of such treatment the size and/or severity of any neuronal damage that develops is minimized.

The disclosure provides prophylactic treatments for neuronal damage including cell death and/or presence of tissue edema and/or cognitive dysfunction and/or cerebral infarcts which may be due to ischemic, hypoxic/anoxic, or hemorrhagic events. An epicatechin, epicatechin derivative alone or in combination with a tetracycline derivative composition of the disclosure can be administered to a subject at risk of experiencing neuronal damage associated or due to a cerebral ischemic condition, and ameliorates the severity of the damage, should it occur. The method is intended for a subject at risk of neuronal damage that is associated with, or results from, an acute or chronic medical condition. Such conditions might arise as a result of medical or surgical treatment planned for the subject (e.g., angioplasty) or as a result of an emergent medical condition such as a stroke or severe blood loss. Other conditions which place a subject at risk for neuronal damage associated with a cerebral ischemic condition include a genetic predisposition to stroke or a condition that is understood to increase the probability of incurring a cerebral infarct such as atherosclerosis, previous stroke or transient ischemic attacks, diabetes mellitus, hypertension, hypercholesterolemia, a history of smoking and may also include schizophrenia, epilepsy, neurodegenerative disorders, Alzheimer's disease and Huntington's disease. Diagnostic and/or pathological characterization of stroke victims has identified numerous additional medical conditions producing stroke that are widely known to practitioners of internal and neurological medicine.

In another aspect, methods of the disclosure relate to preventing myocardial damage in a mammalian subject at risk of developing injury due to a cardiovascular ischemic condition, e.g. for example, by a myocardial infarction or CHF. The methods of reducing myocardial damage relate to minimizing the extent and/or severity of injury in the heart associated with or due to a myocardial ischemic condition by ameliorating or reducing the injury that would otherwise occur. The methods encompass administering an epicatechin, epicatechin derivative alone or in combination with a tetracycline derivative composition to a subject. The amount administered and the duration of the treatment are effective to minimize the size and/or severity of the myocardial damage in the mammalian subject as measured by for example, reduction in myocardial cell death and/or reduction in myocardial edema associated with a myocardial ischemic condition and/or reduction in myocardial infarct size. Thus, it is anticipated that as a result of such treatment the size and/or severity of any myocardial damage that develops is minimized.

The disclosure provides prophylactic treatments for myocardial damage including cell death and/or presence of myocardial edema and/or myocardial infarcts which may be due to ischemic, hypoxic/anoxic, or hemorrhagic events. An epicatechin/epicatechin derivative alone or in combination with a tetracycline derivative composition of the disclosure are administered to a subject at risk of experiencing myocardial damage associated or due to a myocardial ischemic condition, and ameliorates the severity of the damage, should it occur. The method is intended for a subject at risk of myocardial damage that is associated with, or results from, an acute or chronic medical condition. Such conditions might arise as a result of medical or surgical treatment planned for the subject (e.g., angioplasty) or as a result of an emergent medical condition such as a myocardial infarction or severe blood loss. Other conditions which place a subject at risk for myocardial damage associated with a myocardial ischemic condition include a genetic predisposition to myocardial infarction or a condition that is understood to increase the probability of incurring a myocardial infarct such as atherosclerosis, CHF, previous myocardial infarction or transient ischemic attacks, diabetes mellitus, hypertension, hypercholesterolemia, and a history of smoking.

As used herein the phrase "adverse cardiac remodeling" refers to the changes in size, shape, and associated function of the heart after injury to the left and right ventricle and/or right and left atrium. The injury is typically due to acute myocardial infarction (such as, for example transmural or ST segment elevation infarction) or induced injury (such as for example, heart surgery), but may be from a number of causes that result in increased pressure or volume overload (forms of strain) on the heart. Cardiac remodeling includes hypertrophy, thinning of the myocardium, scar formation of the myocardium, atrophy of the myocardium, heart failure progression and combinations thereof. Chronic hypertension, Kawasaki's disease, congenital heart disease with intracardiac shunting, and valvular heart disease may lead to remodeling. Additionally remodeling may stem from coronary artery bypass surgery, cardiac transplant and application of a mechanical support device, such as a left ventricular assist device (LVAD).

As used herein "reduced myocardial infarct size" refers to a decrease in the size of a myocardial infarct in subjects treated with epicatechin compared to the size of a myocardial infarct in control subjects receiving no epicatechin. In the disclosed methods, "reducing" can refer to any one of a 5%, 10%, a 20%, a 30%, a 40%, or even a 50% decrease in myocardial infarct size. Alternately "reducing" can refer to any one of a 60%, 70% or 80% decrease in myocardial infarct size.

As is known to those of skill in the art, changes to the myocardium, particularly determination of the size of a myocardial infarct, can be made using imaging techniques such as echocardiography, cardiac MRI, cardiac CT, and cardiac nuclear scans. Additionally, elevation of one or more biomarkers, including troponin, CK-MB (creatine kinase mb), and CPK (creatine phosphokinase), is known to be indicative of dead or dying myocardium. There is also evidence that the biomarker BNP (B-type Naturetic Peptide) can be used as a marker for cardiac remodeling.

As used herein "favorable cardiac remodeling" refers to preservation of chamber size, shape, function and the prevention of ventricular wall thinning and scarring which occurs after injury to the heart.

As used herein "atrial fibrillation" and "atrial flutter" each refers to an arrhythmia where the atria do not beat effectively in coordination with the ventricle with often an accompanying decrease in cardiac output.

As used herein in reference to heart tissue "induced injury" refers to damaged myocardium, such as damage that results from heart surgery, including but not limited to, coronary artery bypass surgery, cardiac transplant and application of a mechanical support device, such as a left ventricular assist device (LVAD).

As used herein, an "ischemia/reperfusion event" includes, but is not limited to, myocardial ischemia, myocardial reperfusion, subarachnoid hemorrhage, ischemic strokes (including strokes resulting from cerebral thrombosis, cerebral embolism, and atrial fibrillation), hemorrhagic strokes (including strokes resulting from aneurysm and arteriovenous malformation), and transient ischemic attack, cardiac surgery where a heart lung machine is used such as coronary artery bypassing, and preservation of organs for transplant.

As used herein "ischemia/reperfusion injury" refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

Catechins are polyphenolic antioxidant found in plants. Catechins are flavonoids and, to be more specific, flavan-3-ols. Catechin and epicatechin are epimers, with (−)-epicatechin and (+)-catechin being the most common optical isomers found in nature.

Catechins constitute about 25% of the dry weight of fresh tea leaves although total the content varies widely depending on tea variety and growth conditions.

Catechins or Flavanols are found in teas and grapes and include, for example, monomeric flavan-3-ols catechin, epicatechin, gallocatechin, epigallocatechin, and epicatechin 3-O-gallate. Individuals at risk for ischemia/reperfusion events can decrease the risk of necrosis in future events by taking epicatechin, its pharmaceutically acceptable salt, or a derivative thereof (such as, but not limited to, (−)-epigallocatechin (EGC), (−)-epicatechin-3-gallate (ECG) and (−)-epigallocatechin-3-gallate (EGCG)) prophylactically up to an indefinite period of time. It is also understood that many ischemia/reperfusion events have early warning symptoms preceding the actual event which can allow the subject to seek immediate treatment. Even if there is injury caused by future ischemia/reperfusion events, it is contemplated that the prophylactic administration of epicatechin will reduce infarct size and adverse remodeling. For example, disclosed herein are methods of reducing the potential infarct size and adverse remodeling in a subject in need thereof comprising administering to the subject epicatechin at least 30 minutes before a ischemia/reperfusion event. Disclosed herein are methods wherein epicatechin is administered 15, 30 minutes, 1, 2, 6, 12, 24 hour(s), 2, 3 days, 1, or 2 weeks or any time point before the ischemia/reperfusion event.

Ischemia/reperfusion events can occur in subjects who are unaware of the impending infarction or ischemic event. In such individuals, there is a need to reduce the potential infarct size and adverse remodeling. Thus, the methods disclosed herein can be used to reduce the potential infarct size and adverse remodeling following the ischemia/reperfusion event. Thus the disclosed methods of reducing the potential infarct size and adverse remodeling in a subject in need thereof comprise administering to the subject an epicatechin (e.g., such as epigalocatechin), a derivative thereof or a pharmaceutically acceptable salt thereof within 24 hours following the ischemia/reperfusion event. Generally the more quickly epicatechin can be administered following the ischemia/reperfusion event, the less the likelihood of injury and subsequently the greater the potential reduction in infarct size and adverse remodeling. Thus, disclosed herein are methods wherein epicatechin is administered within 24 hours or 12 hours, alternately 6 hours, 2 hours or even 1 hour following the ischemia/reperfusion event. In one embodiment, the epicatechin or derivative thereof (e.g., epigalocatechin) is administered 30 minutes, 15 minutes, 10 minutes or even 5 minutes following the ischemia/reperfusion event.

In yet another embodiment, the epicatechin or derivative thereof (e.g., epigalocatechin) is administered prior to, following or concurrently with the administration of a tetracycline or derivative thereof. Exemplary tetracycline derivatives include, but are not limited to, chlortetracycline, oxytetracycline, demeclocycline, doxycycline, lymecycline, meclocycline, methacycline, minocycline, chlortetracycline, sancycline, chelocardin, apicycline; clomocycline, guamecycline, meglucycline, mepylcycline, penimepicycline, pipacycline, etamocycline, penimocycline and rolitetracycline. In addition, chemically modified tetracyclines can be used in the methods and compositions of the disclosure. Examples of chemically modified tetracyclines (CMTs) include:

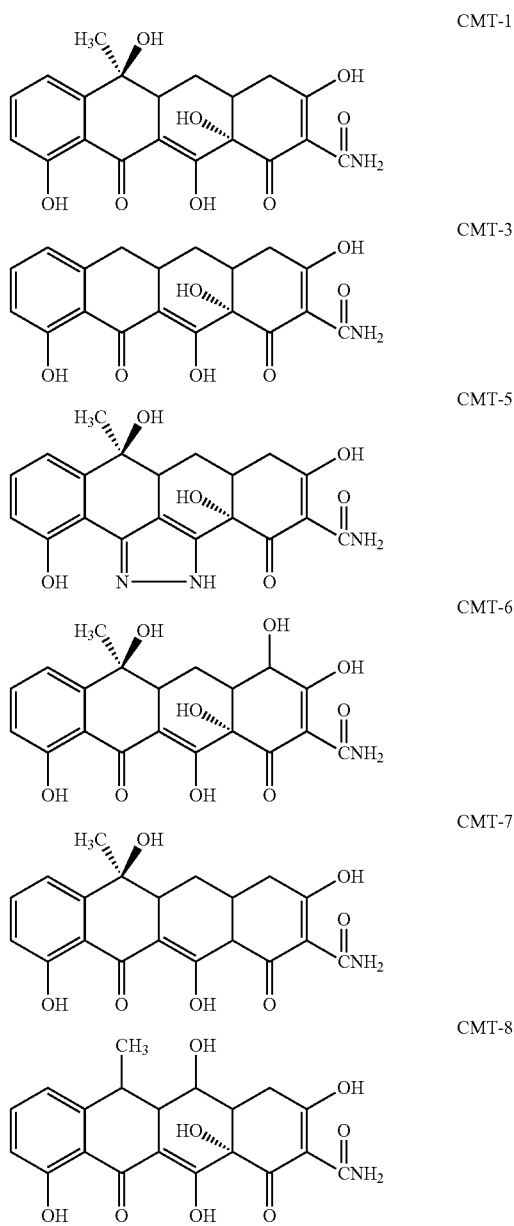

In a further embodiment, the epicatechin or derivative thereof is administered concurrently with a reperfusion/ thrombolytic agents (e.g., a tPA or other reperfusion agent). In yet a further aspect, the epicatechin or derivative thereof is administered prior to or following administration of a reperfusion agents (e.g., tPA). In yet another aspect, where a reperfusion/thrombolytic agent is administered an NMDA receptor antagonist may be administered.

Exemplary thrombolytic agents include alteplase, tenecteplase, reteplase, streptase, abbokinase, pamiteplase, nateplase, desmoteplase, duteplase, monteplase, reteplase, lanoteplase, microplasmin, Bat-tPA, BB-10153, and any combination thereof. Exemplary NMDA receptor antagonists include 3-alpha-ol-5-beta-pregnan-20-one hemisuccinate (ABHS), ketamine, memantine, dextromethorphan, dextrorphan, and dextromethorphan hydrobromide.

The disclosure demonstrates that epicatechin significantly reduces myocardial tissue injury and infarct size secondary to ischemia with both temporary occlusion and permanent occlusion of an artery. These beneficial effects are sustained over time and are independent of changes in blood pressure and occur at very low doses of the compound. Epicatechin also leads to favorable cardiac ventricular remodeling after tissue injury.

In one aspect the disclosure is directed to a method of reducing infarct size in the heart following permanent ischemia or an ischemia/reperfusion event in a subject comprising administering to a subject in need thereof a drug selected from the group consisting of epicatechin, derivatives thereof and pharmaceutically acceptable salts thereof, wherein the subject is a human or a veterinary animal. In one embodiment, the permanent ischemia or ischemia/reperfusion event is a myocardial infarction, unstable angina, or acute coronary syndrome.

Another aspect of the disclosure is a method for reducing myocardial infarct size in a subject for up to at least 3 weeks following myocardial infarction comprising administering to a subject in need thereof a drug selected from the group consisting of epicatechin, derivatives thereof and pharmaceutically acceptable salts thereof, wherein said myocardial infarct size is reduced for up to 3 weeks or longer. In one embodiment the myocardial infarct size is permanently reduced.

In one embodiment of any of the aspects disclosed herein epicatechin or a pharmaceutically acceptable salt thereof is administered after permanent ischemia or the ischemia/reperfusion event. For example epicatechin or a pharmaceutically acceptable salt thereof can be administered within 24 hour(s) following permanent ischemia or the ischemia/reperfusion event. Alternately, epicatechin is administered 1 hour after permanent ischemia or the ischemia/reperfusion event or 6 hours after the event. In another alternative, epicatechin is administered 48 hours after permanent ischemia or the ischemia/reperfusion event. In yet another alternative, epicatechin or a pharmaceutically acceptable salt thereof is administered during permanent ischemia or the ischemia/reperfusion event. In one embodiment of any of the aspects disclosed herein a drug selected from the group consisting of epicatechin, derivatives thereof and pharmaceutically acceptable salts thereof is administered in an amount between about 1 mg/kg/day and about 10 mg/kg/day. Alternately, about 0.75 mg/kg/day is administered, or about 0.5 mg/kg/day. In another alternative, about 10 mg/kg/day or about 15 mg/kg/day or about 20 mg/kg/day is administered. In yet another alternative about 1 mg/kg/day is administered to a subject. In one embodiment of any of the aspects disclosed herein the blood plasma concentration of a drug selected from the group consisting of epicatechin, derivatives thereof and pharmaceutically acceptable salts thereof in a patient is less than about 20 µM. Alternately the blood plasma concentration in a patient is less than about 15 µM or less than about 10 µM. In another variation, the blood plasma level of epicatechin in a patient is greater than 20 µM or greater than 50 µM or even greater than 100 µM.

In one embodiment of any of the aspects disclosed herein, epicatechin or a pharmaceutically acceptable salt thereof is administered in combination with a tetracycline antibiotic or derivative thereof. In one alternative, the tetracycline antibiotic is selected from the group consisting of tetracycline, chlortetracycline, oxytetracycline, demeclocycline, doxycycline, lymecycline, meclocycline, methacycline, minocycline, chlortetracycline, sancycline, chelocardin, apicycline; clomocycline, guamecycline, meglucycline, mepylcycline, penimepicycline, pipacycline, etamocycline, penimocycline, 4-de-dimethylaminotetracycline; CMT-1 and rolitetracycline. Generally, the tetracycline antibiotic is doxycycline; in particular, doxycycline can be conjugated to epicatechin or a pharmaceutically acceptable salt thereof.

In one embodiment, the tetracycline, doxycycline or derivatives thereof are conjugated to a peptide or other desirable molecule (e.g., epicatechin) through a click reaction (see, e.g., Bertozzi, C. et al. PNAS, 2007, vol. 104, no. 43, pp. 16793-16797; H. C. Hang, C. Yu, D. L. Kato, C. R. Bertozzi, Proc. Natl. Acad. Sci. U.S.A. 100, 14846 (2003); D. H. Dube, J. A. Prescher, C. N. Quang, C. R. Bertozzi, Proc. Natl. Acad. Sci. U.S.A. 103, 4819 (2006); P. V. Chang, J. A. Prescher, M. J. Hangauer, C. R. Bertozzi, J. Am. Chem. Soc. 129, 8400 (2007); Scott T. Laughlin, Jeremy M. Baskin, Sharon L. Amacher, Carolyn R. Bertozzi. Science 2008:Vol. 320. no. 5876, pp. 664-667; each incorporated herein by reference; see also the world-wide-web at scripps.edu/chem/sharpless/click.html). In one embodiment, the tetracycline, doxycycline or derivative thereof are conjugated to a cleavable peptide or biomolecule which is conjugated to an epicatechin or derivative thereof. In this aspect, the cleavable biomolecule can be designed to be cleaved in the presence of a ischemic injury site where an enzyme is upregulated due to ischemic injury (e.g., gelatinases and matrix metallo-proteinases). This would allow, for example, selective activation of an epicatechin-doxycycline conjugate at the site of an injury.

Tetracycline derivatives are known in the art. For example, tetracycline derivatives that can be used in the methods and compositions of the disclosure include, but are not limited to, substituted tetracycline compounds or compounds with a similar ring structure to tetracycline. Other derivatives and analogues comprising a four ring structure are also included (See Rogalski, "Chemical Modifications of Tetracyclines," J Periodontal Res. 28 (6 Pt 1):420-8, (1993), the entire contents of which are hereby incorporated herein by reference).

In other cases, the compounds of the disclosure may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the disclosure. These salts can likewise be prepared in situ during the final isolation and purification of the compounds, or by separately reacting the purified compound in its free acid form with a suitable base, such as the hydroxide, carbonate or bicarbonate or a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters.

Another aspect of the disclosure is a method of reducing infarct size in a cardiovascular (e.g., the heart) or neuronal tissue following permanent ischemia or an ischemia/reperfusion event in a subject at risk of having permanent ischemia or an ischemia/reperfusion event, comprising administering to a subject a drug selected from the group consisting of epicatechin, derivatives thereof and pharmaceutically acceptable salts thereof, wherein the subject is a human or a veterinary animal. In a further aspect, the method further comprises administering a tetracycline or derivative thereof (e.g., a doxycycline).

Yet another aspect of the disclosure is a method of treating subarachnoid hemorrhage comprising administering to the subject a drug selected from the group consisting of epicatechin, derivatives thereof and pharmaceutically acceptable salts thereof, wherein the subject is a human or a veterinary animal. In a further aspect, the method further comprises administering a tetracycline or derivative thereof (e.g., a doxycycline).

Still a further aspect of the disclosure is a method of treating atrial fibrillation in a subject comprising administering to a subject in need thereof a drug selected from the group consisting of epicatechin, derivatives thereof and pharmaceutically acceptable salts thereof, wherein the subject is a human or a veterinary animal. In a further aspect, the method further comprises administering a tetracycline or derivative thereof (e.g., a doxycycline).

Another aspect is a method for delaying, attenuating or preventing adverse cardiac remodeling in a subject comprising administering to a subject in need thereof a drug selected from the group consisting of epicatechin, derivatives thereof and pharmaceutically acceptable salts thereof, wherein the subject is a human or a veterinary animal. In one embodiment, the adverse cardiac remodeling is delayed, attenuated or prevented at three weeks after the ischemic event. In another embodiment, the adverse cardiac remodeling is delayed, attenuated or prevented at two months after the ischemic event. In another embodiment, the adverse cardiac remodeling is permanently delayed, attenuated or prevented. Generally, adverse cardiac remodeling comprises hypertrophy, thinning of myocardium, scar formation of myocardium, atrophy of myocardium, heart failure progression or combinations thereof. In one variation, the subject suffers from Kawasaki disease, chronic hypertension, congenital heart disease with intracardiac shunting, congestive heart failure, or valvular heart disease. In another variation, the remodeling stems from coronary artery bypass surgery, cardiac transplant or receipt of a mechanical support device, such as an LVAD. In a further aspect, the method further comprises administering a tetracycline or derivative thereof (e.g., a doxycycline).

Another aspect of the disclosure is a method of enhancing or preserving migration, seeding, proliferation, differentiation and/or survival of stem cells in injured heart tissue of a subject comprising administering to a subject in need thereof a drug selected from the group consisting of epicatechin, derivatives thereof and pharmaceutically acceptable salts thereof. In a further aspect, the method further comprises administering a tetracycline or derivative thereof (e.g., a doxycycline).

In another aspect, the disclosure discloses a method of treating a subject having an induced injury to the heart or suffering from a disease that results from insufficient growth and/or differentiation of stem cells and/or that compromises engraftment of cells in the heart comprising administering to a subject in need thereof a drug selected from the group consisting of epicatechin, derivatives thereof and pharmaceutically acceptable salts thereof. In one variation, the disease is selected from the group consisting of ischemic injury, myocardial infarction, muscle ischemia, heart disease, congenital heart failure, and congestive heart failure. In another variation the induced injury to the heart is selected from the group of coronary artery bypass surgery, cardiac transplant and receipt of a mechanical heart. In a further aspect, the method further comprises administering a tetracycline or derivative thereof (e.g., a doxycycline).

In another aspect of the disclosure, a epicatechin or derivative is administered chronically (1 to 10 mg/kg per day) to patients with atrial fibrillation for favorable remodeling effects.

In another aspect of the disclosure, epicatechin is administered chronically (1 to 10 mg/kg per day) to patients with atrial fibrillation for favorable remodeling effects.

In yet another aspect, epicatechin is administered to patients with vasospasm in subarachnoid hemorrhage. In one embodiment, epicatechin is administered to these patients intrathecally. In another embodiment, in patients with subarachnoid hemorrhage epicatechin is administered intra-arterially, such as when the aneurysm is coiled via endovascular techniques. In yet another embodiment, epicatechin is administered prophylactically to prevent cerebral vasospasm after subarachnoid hemorrhage. In still another embodiment, epicatechin is administered intra-arterially as an adjuvant to calcium channel blockers in the treatment of acute vasospasm in subarachnoid hemorrhage.

In still another aspect, epicatechin is employed as a stem cell proliferation/differentiation promoting agent in the heart. In one embodiment, epicatechin is used to promote the proliferation and differentiation of stem cell populations in the heart. Promoting the proliferation and differentiation of uncommitted stem cell populations may be helpful in the treatment of conditions in which stem cell viability may be compromised, including but not limited to diabetic; viral, and ischemic, non-ischemic cardiomyopathy.

In one aspect of the disclosure, epicatechin is administered in combination with a tetracycline antibiotic. Naturally-occurring members of the tetracycline antibiotic family include tetracycline, chlortetracycline, oxytetracycline, and demeclocycline. Semi-synthetic members of the tetracycline family include doxycycline, lymecycline, meclocycline, methacycline, minocycline, and rolitetracycline. In particular, doxycycline has a novel action in the heart and improves remodeling of heart muscle after a heart attack. Doxycycline is avidly taken up by tissues that have low blood flow (such as heart muscle when blood flow is reduced in the setting of a heart attack). The tetracycline antibiotic, such as doxycycline, may be used as carrier for epicatechin, in which epicatechin is chemically conjugated to a tetracycline antibiotic or derivative thereof, by standard chemical synthetic methods known to those of skill in the chemical arts. In this embodiment, the epicatechin is carried by the tetracycline antibiotic or derivative thereof to areas of the heart where the tissue is injured. In another embodiment, the tetracycline antibiotic or derivative thereof is administered concurrently with epicatechin. In yet another embodiment, the epicatechin is administered before or after administration of the tetracycline antibiotic.

In one variation of any of the embodiments or aspects disclosed herein a drug selected from the group consisting of epicatechin, derivatives thereof and pharmaceutically acceptable salts thereof is administered. In another variation of any of the embodiments or aspects disclosed herein epicatechin or a pharmaceutically acceptable salt thereof is administered. The epicatechin, its derivative or its salt administered via the means disclosed herein can be in any variety of concentrations, combination with other elements or agents, temperatures or other states best suited for the targeted applications.

Compounds of the disclosure are administered orally in a total daily dose of about 0.1 mg/kg/dose to about 100 mg/kg/dose, alternately from about 0.3 mg/kg/dose to about 30 mg/kg/dose. In another embodiment the dose range is from about 0.5 to about 10 mg/kg/day. Alternately about 0.5 to about 1 mg/kg/day is administered. Generally between about 25 mg and about 1 gram per day can be administered; alternately between about 25 mg and about 200 mg can be administered. In one embodiment, the dose of an epicatechin or derivative thereof is about 10 mg/kg/dose or greater. In a further embodiment, the tetracycline derivative such as doxycycline is in a dose of about 2.5 mg/kg/dose or greater. In certain embodiments, epicatechin or derivative thereof at a dose of at least about 10 mg/kg is administered together with a tetracycline derivative such as doxycycline at a dose of at least about 2.5 mg/kg. Such delivery may be by a parenteral route such as intravenous delivery. As discussed herein, such pharmaceutical compositions may be administered within 48 hours of the onset of an ischemic or ischemia/reperfusion event, within 48 hours of initiating a medical procedure, or within 48 hours of presentation for medical treatment; and such administration may be followed by further administrations of one or both of these drug compounds by a parenteral or enteral route. The use of time-release preparations to control the rate of release of the active ingredient may be preferred. The dose may be administered in as many divided doses as is convenient. Such rates are easily maintained when these compounds are intravenously administered as discussed below.

For the purposes of this disclosure, the compounds may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to sublingual and buccal. Oral administration includes fluid drinks, energy bars, as well as pill formulations.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 0.07 to 1.7 mmol (approximately 20 to 500 mg) of active material compounded with an appropriate and convenient amount of carrier material-which may vary from about 5 to about 95% of the total compositions. Typically the pharmaceutical composition be prepared which provides easily measurable amounts for administration.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide. slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Typical unit dosage formulations are those containing a daily dose or unit, daily sub-dose, or an appropriate fraction thereof, epicatechin.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

Analogously, derivatives of epicatechin are known to those of skill in the chemical arts. Such derivatives include, but are not limited to, epigallocatechin, epicatechin-3-gallate, and epigallocatechin-3-gallate.

As used herein, the term "an ischemic injury alleviating amount" or "effective amount" means the amount of a composition comprising an epicatechin or derivative thereof (e.g., epigalocatechin) either alone or in combination with a tetracycline or derivative thereof (e.g., doxycyline) useful for causing a diminution in tissue damage. An effective amount to be administered systemically depends on the body weight of the subject. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian.

The disclosure also provides biomarkers for determining the diagnosis, prognosis and/or efficacy of a treatment of the disclosure. A biomarker refers to a detectable biological entity associated with a particular phenotype or risk of developing a particular phenotype. The biological entity can be a polypeptide or polynucleotide. A biomarker to be detected is referred to as a target. For example, a target polynucleotide refers to a biomarker comprising a polynucleotide (e.g., an mRNA or cDNA) that is to be detected. In another example, a target polypeptide refers to a protein expressed (i.e., transcribed and translated) that is to be detected. A biomarker, as defined by the National Institutes of Health (NIH), refers to a molecular indicator of a specific biological property; a biochemical feature or facet that can be used to measure the progress of disease or the effects of treatment. A panel of biomarkers is a selection of at least two biomarkers. Biomarkers may be from a variety of classes of molecules.

A gene refers to a segment of genomic DNA that contains the coding sequence for a protein, wherein the segment may include promoters, exons, introns, and other untranslated regions that control expression.

A genotype is an unphased 5' to 3' sequence of nucleotide pair(s) found at a set of one or more polymorphic sites in a locus on a pair of homologous chromosomes in an individual. As used herein, genotype includes a full-genotype and/or a sub-genotype.

Genotyping is a process for determining a genotype of an individual.

A haplotype is a 5' to 3' sequence of nucleotides found at a set of one or more polymorphic sites in a locus on a single chromosome from a single individual.

Haplotype pair is two haplotypes found for a locus in a single individual.

Haplotyping is the process for determining one or more haplotypes in an individual and includes use of family pedigrees, molecular techniques and/or statistical inference.

A genetic locus refers to a location on a chromosome or DNA molecule corresponding to a gene or a physical or phenotypic feature, where physical features include polymorphic sites.

Polymorphic site (PS) is a position on a chromosome or DNA molecule at which at least two alternative sequences are found in a population.

A polymorphism refers to the sequence variation observed in an individual at a polymorphic site. Polymorphisms include nucleotide substitutions, insertions, deletions and microsatellites and may, but need not, result in detectable differences in gene expression or protein function. A single nucleotide polymorphism (SNP) is a single change in the nucleotide variation at a polymorphic site.

An oligonucleotide probe or a primer refers to a nucleic acid molecule of between 8 and 2000 nucleotides in length, or is specified to be about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under, a particular set of conditions may be empirically determined by one of skill in the art.

Oligonucleotide primers and probes can be prepared by any suitable method, including, for example, cloning and restriction of appropriate sequences and direct chemical synthesis. The oligonucleotide primers and probes can contain conventional nucleotides, as well as any of a variety of analogs. For example, the term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-($C_1$-$C_6$)alkoxyribose, 2'-($C_5$-$C_{14}$)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$) alkylribose, 2'-deoxy-3'-($C_1$-$C_6$)-alkoxyribose and 2'-deoxy-3'-($C_5$-$C_{14}$)aryloxyribose, ribose, 2'-deoxyribose, 2',3'-dideoxyribose, 2'-haloribose, 2-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352 and WO 99/14226). Exemplary LNA sugar analogs within a polynucleotide include, but are not limited to, the structures: where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N_9$-position of the nucleotide base. When the nucleotide base is pyrimidine, e.g. C, T or U, the pentose sugar is attached to the $N_1$-position of the nucleotide base, except for pseudouridines, in which the pentose sugar is attached to the $C_5$ position of the uracil nucleotide base (see, e.g., Kornberg and Baker, (1992) DNA Replication, 2nd Ed., Freeman, San Francisco, Calif.). The 3' end of the probe can be functionalized with a capture or detectable label to assist in detection of a target polynucleotide or of a polymorphism.

Any of the oligonucleotides or nucleic acids of the disclosure can be labeled by incorporating a detectable label measurable by spectroscopic, photochemical, biochemical, immunochemical, or chemical means. For example, such labels can comprise radioactive substances (e.g., $^{32}$P, $^{35}$S, $^{3}$H, $^{125}$I), fluorescent dyes (e.g., 5-bromodesoxyuridin, fluorescein, acetylaminofluorene, digoxigenin), biotin, nanoparticles, and the like. Such oligonucleotides are typically labeled at their 3' and 5' ends.

A probe refers to a molecule which can detectably distinguish changes in gene expression or can distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include antibody binding and nucleic acid probe hybridization. Thus, for example, probes can include enzyme substrates, antibodies and antibody fragments, and nucleic acid hybridization probes (including primers useful for polynucleotide amplification and/or detection). Thus, in one embodiment, the detection of the presence or absence of the at least one target polynucleotide involves contacting a biological sample with a probe, typically an oligonucleotide probe, where the probe hybridizes with a form of a target polynucleotide in the biological sample containing a complementary sequence, where the hybridization is carried out under selective hybridization conditions. Such an oligonucleotide probe can include one or more nucleic acid analogs, labels or other substituents or moieties so long as the base-pairing function is retained.

A reference or control population refers to a group of subjects or individuals who are predicted to be representative of the genetic variation found in the general population having a particular genotype or expression profile. Typically, the reference population represents the genetic variation in the population at a certainty level of at least 85%, typically at least 90%, least 95% and but commonly at least 99%.

A subject comprises an individual (e.g., a mammalian subject or human) whose gene expression profile, genotypes or haplotypes or response to treatment or disease state are to be determined.

The disclosure includes methods of screening a subject for responsiveness to an epicatechin comprising measuring expression or a single nucleotide polymorphism in an eNOS gene. SNPs for eNOS are known to those of skill in the art. Probes and oligonucleotide primers comprising sequences including the SNP can be used to determine the presence or absence of such genes in a subject.

The disclosure also comprises a method of detecting a biomarker or panel of biomarkers associated with a determining or assessing the efficacy of an epicatechin and doxycycline (or derivative thereof) in a subject.

For example, the following biomarkers can be used to assess efficacy of epicatechin and doxycycline and also help determine which patients would receive most benefit from a composition of the disclosure: markers of inflammation and hemodynmic stress ST2, GD-15 and BNP; markers of collagen biosynthesis: procollagen type I (PIP) the propeptide of procollagen type III (p-III NP); and markers of oxidative stress: uric acid, FRAP, TRAP, myeloperoxidare. The sequences of such genes, polynucleotide and polypeptides are known and readily available to those of skilled in the art.

Methods known in the art can be used to quantitatively measure the amount of mRNA transcribed by cells present in a sample. Examples of such methods include quantitative polymerase chain reaction (PCR), northern and southern blots. PCR allows for the detection and measurement of very low quantities of mRNA using an amplification process. Genes may either be up regulated or down regulated in any particular biological state, and hence mRNA levels shift accordingly.

In one embodiment, a method for gene expression profiling comprises measuring mRNA levels for biomarkers selected in a panel. Such a method can include the use of primers, probes, enzymes, and other reagents for the preparation, detection, and quantitation of mRNA.

Though a number of detection schemes are contemplated, as will be discussed in more detail below, one method contemplated for detection of polynucleotides is fluorescence spectroscopy, and therefore labels suited to fluorescence spectroscopy are desirable for labeling polynucleotides. One example of such a fluorescent label is SYBR Green, though numerous related fluorescent molecules are known including, without limitation, DAPI, Cy3, Cy3.5, Cy5, CyS.5, Cy7, umbelliferone, fluorescein, fluorescein isothiocyanate (FITC), rhodamine, dichlorotriazinylamine fluorescein, dansyl chloride or phycoerythrin.

Any of the oligonucleotide primers and probes of the disclosure can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers of the disclosure can be attached to or immobilized on a solid support individually or in groups of about 2-10,000 distinct oligonucleotides of the disclosure to a single solid support.

A substrate comprising a plurality of oligonucleotide primers or probes of the disclosure may be used either for detecting or amplifying targeted sequences. The oligonucleotide probes and primers of the disclosure can be attached in contiguous regions or at random locations on the solid support. Alternatively the oligonucleotides of the disclosure may be attached in an ordered array wherein each oligonucleotide is attached to a distinct region of the solid support which does not overlap with the attachment site of any other oligonucleotide. Typically, such oligonucleotide arrays are "addressable" such that distinct locations are recorded and can be accessed as part of an assay procedure. The knowledge of the location of oligonucleotides on an array make "addressable" arrays useful in hybridization assays. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis.

The immobilization of arrays of oligonucleotides on solid supports has been rendered possible by the development of a technology generally referred to as "Very Large Scale Immobilized Polymer Synthesis" in which probes are immobilized in a high density array on a solid surface of a chip (see, e.g., U.S. Pat. Nos. 5,143,854; and 5,412,087 and in PCT Publications WO 90/15070, WO 92/10092 and WO 95/11995, each of which are incorporated herein by reference), which describe methods for forming oligonucleotide arrays through techniques such as light-directed synthesis techniques.

In another aspect, an array of oligonucleotides complementary to subsequences of the target gene is used to determine the identity of the target, measure its amount, and detect differences between the target and a reference wild-type sequence.

Hybridization techniques can also be used to identify the biomarkers and/or polymorphisms of the disclosure. In this aspect, expression profiles or polymorphism(s) are identified based upon the higher thermal stability of a perfectly matched probe compared to the mismatched probe. The hybridization reactions may be carried out in a solid support (e.g., membrane or chip) format, in which, for example, the target nucleic acids are immobilized on nitrocellulose or nylon membranes and probed with oligonucleotide probes of the disclosure. Any of the known hybridization formats may be used, including Southern blots, slot blots, "reverse" dot blots, solution hybridization, solid support based sandwich hybridization, bead-based, silicon chip-based and microtiter well-based hybridization formats.

Hybridization of an oligonucleotide probe to a target polynucleotide may be performed with both entities in solution, or such hybridization may be performed when either the oligonucleotide or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the disclosure include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

In one aspect, a sandwich hybridization assay comprises separating the variant and/or wild-type target nucleic acid biomarker in a sample using a common capture oligonucleotide immobilized on a solid support and then contact with specific probes useful for detecting the variant and wild-type nucleic acids. The oligonucleotide probes are typically tagged with a detectable label.

Hybridization assays based on oligonucleotide arrays rely on the differences in hybridization stability of short oligonucleotides to perfectly matched and mismatched target variants. Each DNA chip can contain thousands to millions of individual synthetic DNA probes arranged in a grid-like pattern and miniaturized to the size of a dime or smaller. Such a chip may comprise oligonucleotides representative of both a wild-type and variant sequences.

Oligonucleotides of the disclosure can be designed to specifically hybridize to a target region of a polynucleotide. As used herein, specific hybridization means the oligonucleotide forms an anti-parallel double-stranded structure with the target region under certain hybridizing conditions, while failing to form such a structure when incubated with a different target polynucleotide or another region in the polynucleotide or with a polynucleotide lacking the desired locus under the same hybridizing conditions. Typically, the oligonucleotide specifically hybridizes to the target region under conventional high stringency conditions.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, in Sambrook et al., Molecular Cloning, A Laboratory Manual, 2nd ed., Cold Spring Harbor Press, Cold Spring Harbor, N.Y. (1989), and in Haymes et al., Nucleic Acid Hybridization, A Practical Approach, IRL Press, Washington, D.C. (1985). While perfectly complementary oligonucleotides are used in most assays for detecting target polynucleotides or polymorphisms, departures from complete complementarity are contemplated where such departures do not prevent the molecule from specifically hybridizing to the target region. For example, an oligonucleotide primer may have a non-complementary fragment at its 5' or 3' end, with the remainder of the primer being complementary to the target region. Those of skill in the art are familiar with parameters that affect hybridization; such as temperature, probe or primer length and composition, buffer composition and salt concentration and can readily adjust these parameters to achieve specific hybridization of a nucleic acid to a target sequence.

A variety of hybridization conditions may be used in the disclosure, including high, moderate and low stringency conditions; see for example Maniatis et al., Molecular Cloning: A Laboratory Manual, 2d Edition, 1989, and Short Protocols in Molecular Biology, ed. Ausubel, et al., hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the polyadenylated mRNA target sequence at equilibrium (as the target sequences are present in excess, at $T_m$, 50% of, the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of helix destabilizing agents such as formamide. The hybridization conditions may also vary when a non-ionic backbone, i.e., PNA is used, as is known in the art. In addition, cross-linking agents may be added after target binding to cross-link, i.e., covalently attach, the two strands of the hybridization complex.

Methods and compositions of the disclosure are useful for diagnosing or determining the efficacy a treatment may have on a subject. Such tests can be performed using DNA or RNA samples collected from blood, cells, tissue scrapings or other cellular materials, and can be performed by a variety of methods including, but not limited to, hybridization with biomarker-specific probes, enzymatic mutation detection, chemical cleavage of mismatches, mass spectrometry or DNA sequencing, including minisequencing. Diagnostic tests may involve a panel of one or more genetic markers (gene expression profiles), often on a solid support, or using PCR techniques, which enables the simultaneous determination of more than one variance in one or more genes or expression of one or more genes.

A target biomarker or region(s) thereof (e.g., containing a polymorphism of interest) may be amplified using any oligonucleotide-directed amplification method including, but not limited to, polymerase chain reaction (PCR) (U.S. Pat. No. 4,965,188), ligase chain reaction (LCR) (Barany et al., Proc. Natl. Acad. Sci. USA 88:189-93 (1991); WO 90/01069), and oligonucleotide ligation assay (OLA) (Landegren et al., Science 241:1077-80 (1988)). Other known nucleic acid amplification procedures may be used to amplify the target region(s) including transcription-based amplification systems (U.S. Pat. No. 5,130,238; European Patent No. EP 329, 822; U.S. Pat. No. 5,169,766; WO 89/06700) and isothermal methods (Walker et al., Proc. Natl. Acad. Sci. USA 89:392-6 (1992)).

Ligase Chain Reaction (LCR) techniques can be used and are particularly useful for detection of polymorphic variants. LCR occurs only when the oligonucleotides are correctly base-paired. The Ligase Chain Reaction (LCR), which utilizes the thermostable Taq ligase for ligation amplification, is useful for interrogating loci of a gene.

In one embodiment, the two hybridization probes are designed each with a target specific portion. The first hybridization probe is designed to be substantially complementary to a first target domain of a target polynucleotide (e.g., a polynucleotide fragment) and the second hybridization probe is substantially complementary to a second target domain of a target polynucleotide (e.g., a polynucleotide fragment). In general, each target specific sequence of a hybridization probe is at least about 5 nucleotides long, with sequences of about 15 to 30 being typical and 20 being especially common. In one embodiment, the first and second target domains are directly adjacent, e.g., they have no intervening nucleotides. In this embodiment, at least a first hybridization probe is hybridized to the first target domain and a second hybridization probe is hybridized to the second target domain. If perfect complementarity exists at the junction, a ligation structure is formed such that the two probes can be ligated together to form a ligated probe. If this complementarity does not exist (due to mismatch based upon a variant), no ligation structure is formed and the probes are not ligated together to an appreciable degree. This may be done using heat cycling, to allow the ligated probe to be denatured off the target polynucleotide such that it may serve as a template for further reactions. The method may also be done using three hybridization probes or hybridization probes that are separated by one or more nucleotides, if dNTPs and a polymerase are added (this is sometimes referred to as "Genetic Bit" analysis).

Analysis of point mutations (e.g., polymorphic variants) in DNA can also be carried out by using the polymerase chain reaction (PCR) and variations thereof. Mismatches can be detected by competitive oligonucleotide priming under hybridization conditions where binding of the perfectly matched primer is favored. In the amplification refractory mutation system technique (ARMS), primers are designed to have perfect matches or mismatches with target sequences either internal or at the 3' residue (Newton et al., Nucl. Acids. Res. 17:2503-2516 (1989)). Under appropriate conditions, only the perfectly annealed oligonucleotide functions as a primer for the PCR reaction, thus providing a method of discrimination between normal and variant sequences.

Single nucleotide primer-guided extension assays can also be used, where the specific incorporation of the correct base is provided by the fidelity of a DNA polymerase. Detecting the nucleotide or nucleotide pair at a polymorphic site of interest may also be determined using a mismatch detection technique including, but not limited to, the RNase protection method using riboprobes (Winter et al., Proc. Natl. Acad. Sci. USA 82:7575 (1985); Meyers et al., Science 230:1242 (1985)) and proteins which recognize nucleotide mismatches, such as the *E. coli* mutS protein (Modrich, Ann. Rev. Genet. 25:229-53 (1991)). Alternatively, variant alleles can be identified by single strand conformation polymorphism (SSCP) analysis (Orita et al., Genomics 5:874-9 (1989); Humphries et al., in MOLECULAR DIAGNOSIS OF GENETIC DISEASES, Elles, ed., pp. 321-340, 1996) or denaturing gradient gel electrophoresis (DGGE) (Wartell et al., Nucl. Acids Res. 18:2699-706 (1990); Sheffield et al., Proc. Natl. Acad. Sci. USA 86:232-6 (1989)).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al., 1989, supra; Ruano et al., 1991, supra; WO 93/22456; Turki et al., J. Clin. Invest. 95:1635-41 (1995)).

Another technique, which may be used to analyze gene expression and polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Quantitative PCR and digital PCR can be used to measure the level of a polynucleotide in a sample. Digital Polymerase Chain Reaction (digital PCR, dPCR or dePCR) can be used to directly quantify and clonally amplify nucleic acids including DNA, cDNA or RNA. Digital PCR amplifies nucleic acids by temperature cycling of a nucleic acid molecule with a DNA polymerase. The reaction is typically carried out in the dispersed phase of an emulsion capturing each individual nucleic acid molecule present in a sample within many separate chambers or regions prior to PCR amplification. A count of chambers containing detectable levels of PCR end-product is a direct measure of the absolute nucleic acids quantity.

Quantitative polymerase chain reaction (qPCR) is a modification of the polymerase chain reaction and real-time quantitative PCR are useful for measuring the amount of DNA after each cycle of PCR by use of fluorescent markers or other detectable labels. Quantitative PCR methods use the addition of a competitor RNA (for reverse-transcriptase PCR) or DNA in serial dilutions or co-amplification of an internal control to ensure that the amplification is stopped while in the exponential growth phase.

Modifications of PCR and PCR techniques are routine in the art and there are commercially available kits useful for PCR amplification.

The detectable label may be a radioactive label or may be a luminescent, fluorescent of enzyme label. Indirect detection processes typically comprise probes covalently labeled with a hapten or ligand such as digoxigenin (DIG) or biotin. In one aspect, following the hybridization step, the target-probe duplex is detected by an antibody- or streptavidin-enzyme complex. Enzymes commonly used in DNA diagnostics are horseradish peroxidase and alkaline phosphatase. Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes.

Examples of detection modes contemplated for, the disclosed methods include, but are not limited to, spectroscopic techniques, such as fluorescence and UV-Vis spectroscopy, scintillation counting, and mass spectroscopy. Complementary to these modes of detection, examples of labels for the purpose of detection and quantitation used in these methods include, but are not limited to, chromophoric labels, scintillation labels, and mass labels. The expression levels of polynucleotides and polypeptides measured using these methods may be normalized to a control established for the purpose of the targeted determination.

Label detection will be based upon the type of label used in the particular assay. Such detection methods are known in the art. For example, radioisotope detection can be performed by autoradiography, scintillation counting or phosphor imaging. For hapten or biotin labels, detection is with an antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitropheny phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or polaroid film or by using single photon counting luminometers.

It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular disease undergoing therapy, as is well understood by those skilled in the art.

EXAMPLES

Results have shown that the cocoa derived flavanol epicatechin (when given at low doses of 1 mg/kg per day) has the ability to protect heart muscle from death when blood flow to heart is temporarily or permanently interrupted. This effect is sustained over time. The doses of epicatechin administered as described herein are below the threshold where its antioxidant properties have been observed.

Example 1

Adult male Sprague-Dawley rats (Harlan, Indianapolis, Ind.) weighing ~250 g were used. Epicatechin (1 mg/kg/day; Sigma-Aldrich, St. Louis, Mo.) or vehicle (water) was administered orally by gavage once/day beginning 10 days before thoracotomy and continuing until the time of the terminal study (48 h or 3 weeks). A subgroup of "normal" animals were treated with water or epicatechin for 10 day and were used to evaluate the effects of epicatechin on hemodynamics. For 48 hr studies the groups included IR and IR+10 day epicatechin. For 3 week studies, the groups included sham, sham+10 day epicatechin, IR and IR+10 day epicatechin.

Ischemia-reperfusion: Animals were anesthetized by intraperitoneal injection of ketamine (100 mg/kg) and xylazine (10 mg/kg), intubated, and positive-pressure ventilated. Following a left thoracotomy, the left anterior descending coronary artery was ligated for 45 min, (except in shams) released and the suture left in place. The chest was closed and animals allowed to fully recover. Successful occlusion and reperfusion were verified by visual inspection of left ventricle (LV) color. Sham animals were treated identically, except the ligature was not tightened.

Hemodynamics: All animals were weighed and anesthetized with 5% isoflurane (maintenance at 1-2%). Arterial (carotid) and LV pressures were measured using a micromanometer just prior to sacrifice and data digitally recorded.

Tissue Collection: At 48 hr post-I/R, the hearts were rapidly excised and perfused with cold cardioplegia. LV freewall (ischemic region) and septum were separated and homogenized on ice in lysis buffer (50 mmol/L Tris pH 7.4, 150 mmol/L NaCl, 5 mmol/L CaCl2, 0.2 mmol/L NaN3, 0.1% Triton X-100). Lysates were cleared by centrifugation at 12,000 g for 10 min. at 4° C.

Determination of Infarct Size: Terminal study hearts were excised and weighed. In 48 h hearts, the area at risk was determined by the reocclusion of the snare and infusion of trypan blue (0.4%) into the cannulated aorta. Hearts were sectioned at 0 mmHg into five 2 mm rings and stained using triphenyltetrazolium chloride to determine the infarct area. Computer assisted image analysis was used using blinded operators. For 3 week studies hearts were processed as above and sectioned to identify the infarct (i.e. scar) area. The images of unfixed, stained rings were also used to measure internal and external chamber diameters, anterior and septal wall thicknesses.

Gelatin Zymography: Gelatin zymography was performed as previously described (21). An internal control (human MMP-2/MMP-9, Chemicon, Temecula, Calif.) was loaded to normalize between gels. Bands of gelatinolytic activity were digitally quantified (Kodak 1D, Eastman Kodak, Rochester, N.Y.).

Myeloperoxidase (MPO) Assay: The MPO assay was performed as previously described with modifications (21). Tissue samples were homogenized in MPO lysis buffer (50 mmol/L KH2PO4 pH 6.0, 0.5% hexadecyltrimethylammonium bromide) and incubated on ice for 30 min. Following centrifugation, the supernatants were reacted with 0.4 mmol/L tetramethylbenzidine (Sigma) and 0.006% H2O2 in 50 mmol/L phosphate at pH 6.0. Absorbance was monitored and MPO activity expressed as mOD/min per gram of protein.

Oxidative stress (reduced glutathione): Oxidized glutathione (GSSG) will be measured by masking the reduced glutathione (GSH) with 2-vinyl pyridine in the enzymatic assay. The ratio GSH/GSSG will be calculated as total tissue oxidative stress.

Statistical Analysis Comparisons between means±S.E.M were analyzed by student's t-tests or one-way ANOVA followed by Bonferroni post-hoc. P<0.05 was considered statistically significant. The investigator who analyzed the data was blinded to what group (control vs. treatment with epicatechin) the animal belonged to.

Hemodynamics: Hemodynamics (Table 1A) were measured in normal and normal+10 d epicatechin. Values recorded 48 h after IR demonstrate no significant changes in either heart rate, LV end-diastolic/peak systolic pressure, or mean aortic pressure between IR groups. In 3 week studies hemodynamic parameters were recorded in sham and IR animals and results were comparable between untreated vs. treated groups (Table 1B). Values shown are mean ±SEM. Statistical analysis was done by ANOVA except where denoted. In the IR group the rats are fed the control and ischemia is induced (by temporary occlusion of the coronary artery). In the IR+epicatechin the rats are given epicatechin and ischemia is induced. Normal rats and normal rats given epicatechin do not have any induced ischemia (i.e. no occlusion of the artery). The purpose of these two groups was to determine baseline hemodynamics.

TABLE 1A

Hemodynamic data obtained from normal, sham, 48 hours ischemia reperfusion (IR) groups. Epicatechin groups were pretreated for 10 days.

| 48 h IR | Normal | Normal + epicatechin | IR | IR + epicatechin |
| --- | --- | --- | --- | --- |
| Group Size | 6 | 6 | 8 | 8 |
| HR (bpm) | 298 ± 17 | 346 ± 8 | 368 ± 12* | 373 ± 17* |
| LVPSP (mmHg) | 125 ± 8 | 112 ± 14 | 102 ± 6 | 110 ± 5 |
| LVEDP (mmHg) | 7.6 ± 0.9 | 6.7 ± 1.3 | 5 ± 0.3 | 4.9 ± 0.5 |
| MAP (mm Hg) | 101 ± 7 | 99 ± 10 | 89 ± 3 | 90 ± 5 |

*$P < 0.05$ vs normal.

HR = heart rate, LVPSP = left ventricular peak systolic pressure, LVEDP = left ventricular end diastolic pressure, MAP = mean aortic pressure. Values shown are mean ± SEM.

TABLE 1B

Hemodynamic and morphometry data obtained from normal, sham, 3 weeks ischemia reperfusion (IR) groups. Epicatechin groups were pretreated for 10 days.

| 3 wk IR | Sham | Sham + epicatechin | IR | IR + epicatechin |
|---|---|---|---|---|
| Group Size | 5 | 3 | 9 | 6 |
| HR (bpm) | 318 ± 12 | 328 ± 11 | 290 ± 6 | 302 ± 18 |
| LVPSP (mmHg) | 119 ± 2.2 | 116 ± 6.2 | 108 ± 2 | 108 ± 4 |
| LVEDP (mmHg) | 6.9 ± 1.1 | 2.6 ± 0.2 | 6.1 ± 0.8 | 5.5 ± 1.5 |
| MAP (mmHg) | 94 ± 4.7 | 92 ± 11 | 89 ± 2 | 85 ± 4 |
| Group Size | 5 | 4 | 7 | 8 |
| HW/BW | 3.2 ± 0.2 | 3.2 ± 0.5 | 4.5 ± 0.2# | 4.5 ± 0.2# |
| Outer LV diam. (mm) | 1.6 ± 0.1 | 1.6 ± 0.1 | 1.6 ± 0.06 | 1.6 ± 0.04 |
| Inner LV diam. (mm) | 0.53 ± 0.02 | 0.52 ± 0.08 | 0.52 ± 0.06 | 0.55 ± 0.05 |
| AW thickness (mm) | 0.52 ± 0.05 | 0.53 ± 0.05 | 0.4 ± 0.3@ | 0.41 ± 0.02 |
| SW thickness (mm) | 0.49 ± 0.05 | 0.47 ± 0.04 | 0.62 ± 0.04 | 0.49 ± 0.03 |

*$P < 0.05$ vs normal,
$P < 0.01$ vs sham,
@$p < 0.01$ vs IR SW thickness (t-test).
HR = heart rate, LVPSP = left ventricular peak systolic pressure, LVEDP = left ventricular end diastolic pressure, MAP = mean aortic pressure, HW/BW = heart weight/body weight. Values shown are mean ± SEM.

Figure 2A:
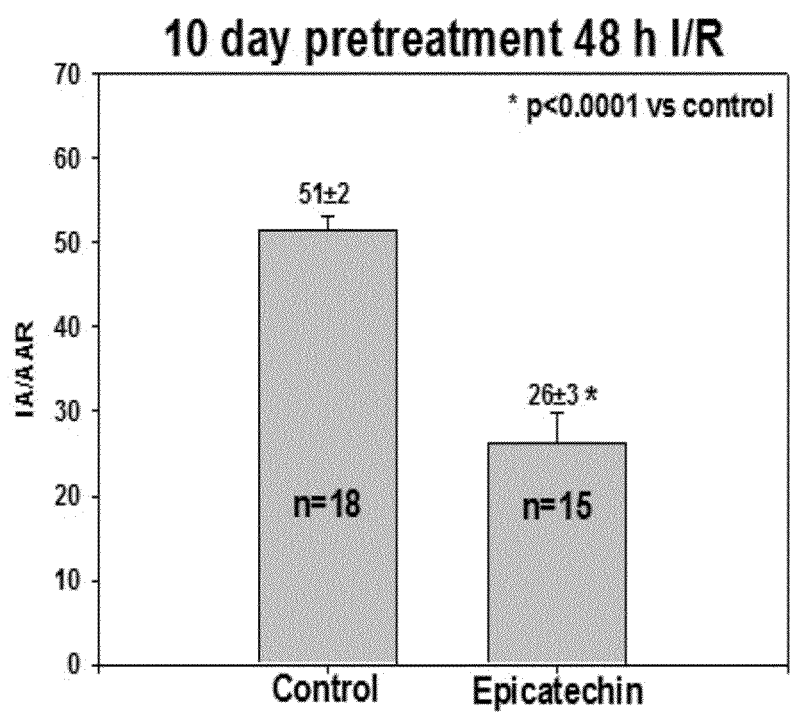
FIG. 2A is a bar graph of the average and mean±SEM values recorded for infarct size in control and epicatechin treated animals 48 h after IR in the temporary occlusion experiment.
Figure 2B:
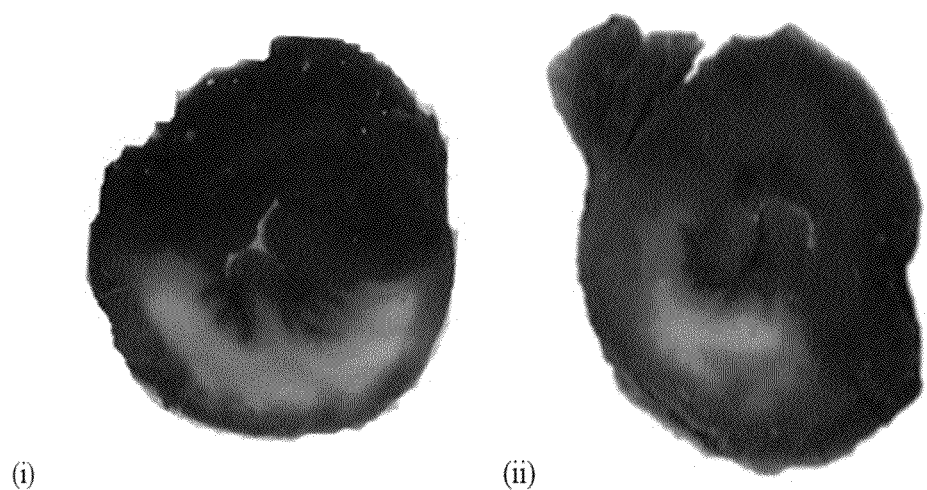
FIG. 2B are representative images of cross sections of hearts stained for infarct size determination in the temporary occlusion experiment: (i) the heart of a control animal; (ii) the heart of an animal pre-treated with epicatechin. The area of infarction is represented by the white color and this is significantly less in the heart of the animal treated with epicatechin.
Figure 3:
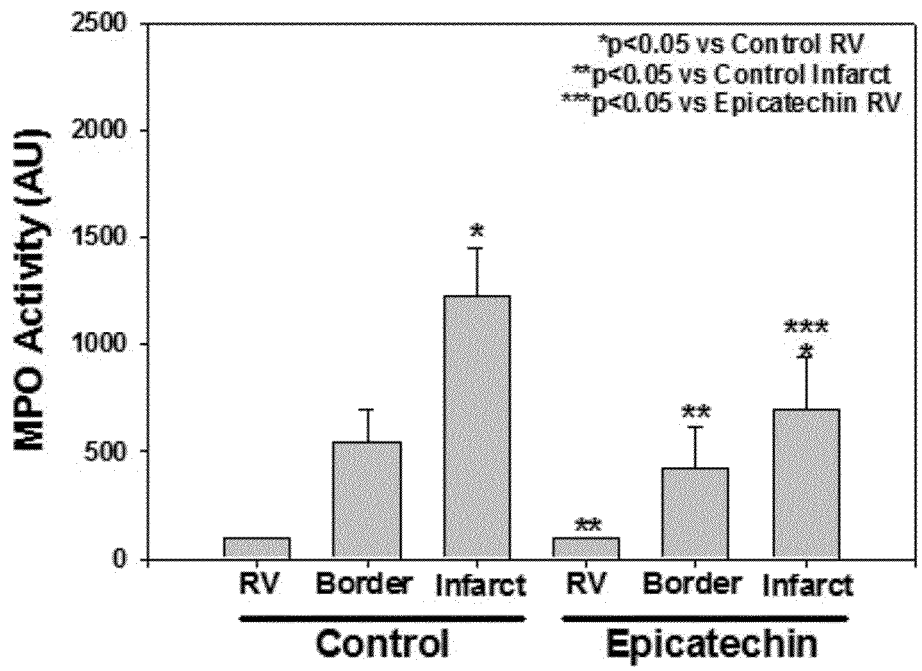
FIG. 3 is a graph of Myeloperoxidase (MPO) levels measured in tissue samples obtained from the right ventricle (RV), border regions and infarcted regions of the left ventricle in control (n=8) and epicatechin (n=8) treated animals. As can be observed epicatechin treated animals demonstrated sustained levels of inflammation in injured tissue as controls.
Figure 4:
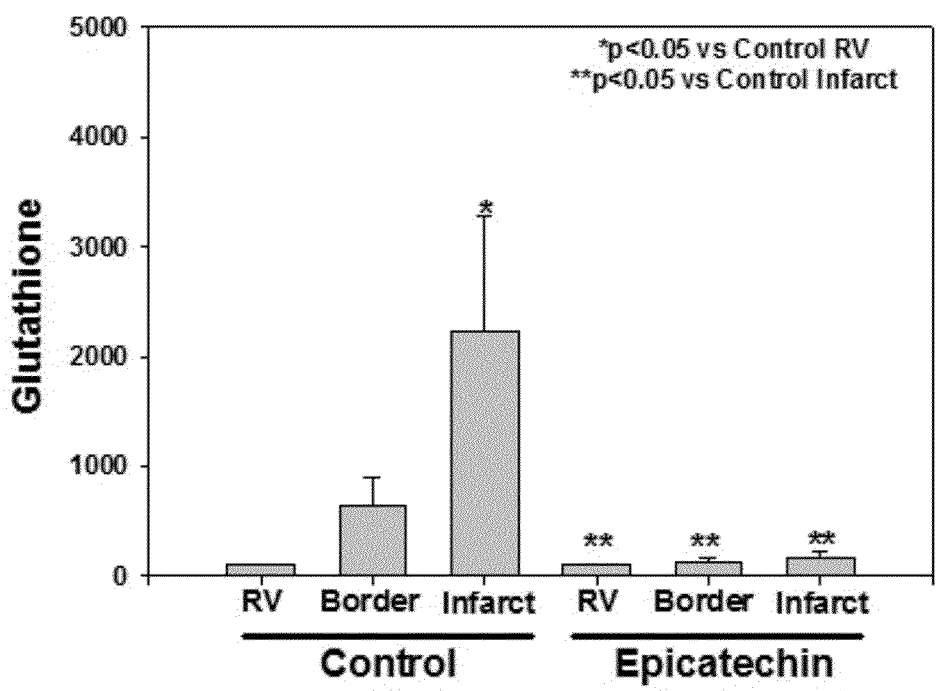
FIG. 4 is a bar graph of Glutathione (oxidative tissue stress in arbitrary units) levels measured in myocardial samples obtained from the right ventricle (RV), border regions and infarcted regions of the left ventricle in control (n=8) and epicatechin (n=8) treated animals. As can be observed epicatechin treatment significantly suppressed levels of tissue oxidative stress.
Figure 5:
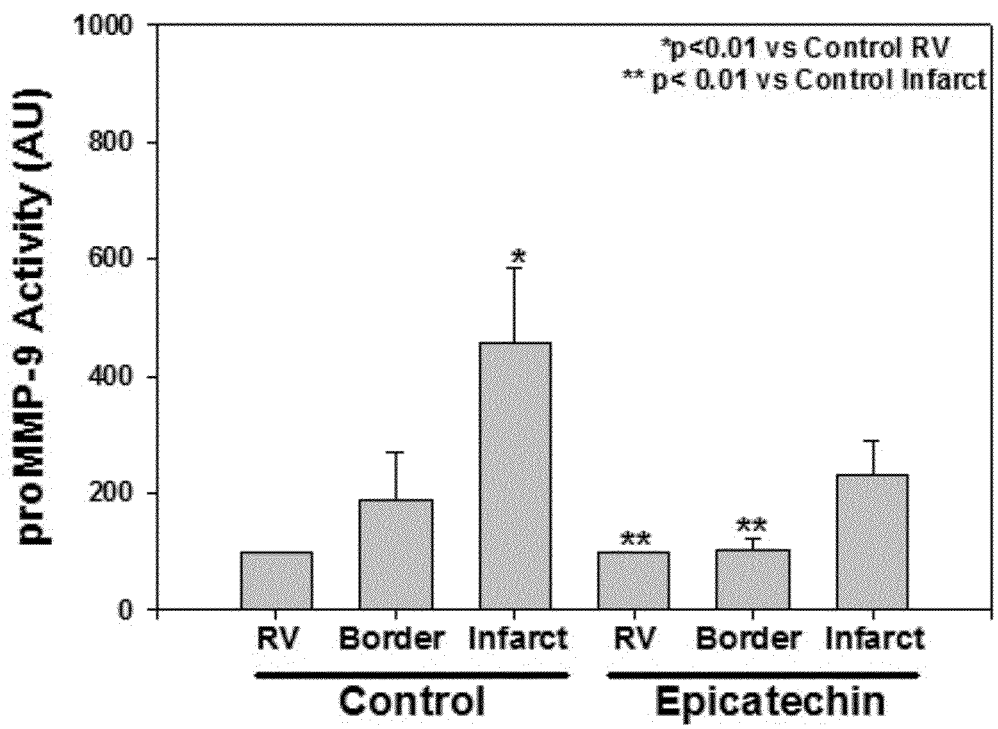
FIG. 5 is a graph of Matrix metalloproteinase-9 (pro-MMP-9 in arbitrary units:AU) levels measured in myocardial samples obtained from the right ventricle (RV), border regions and infarcted regions of the left ventricle in control (n=8) and epicatechin (n=8) treated animals. As can be observed epicatechin treatment led to suppressed levels of metalloproteinase activity in infarcted tissue.
Figure 6:
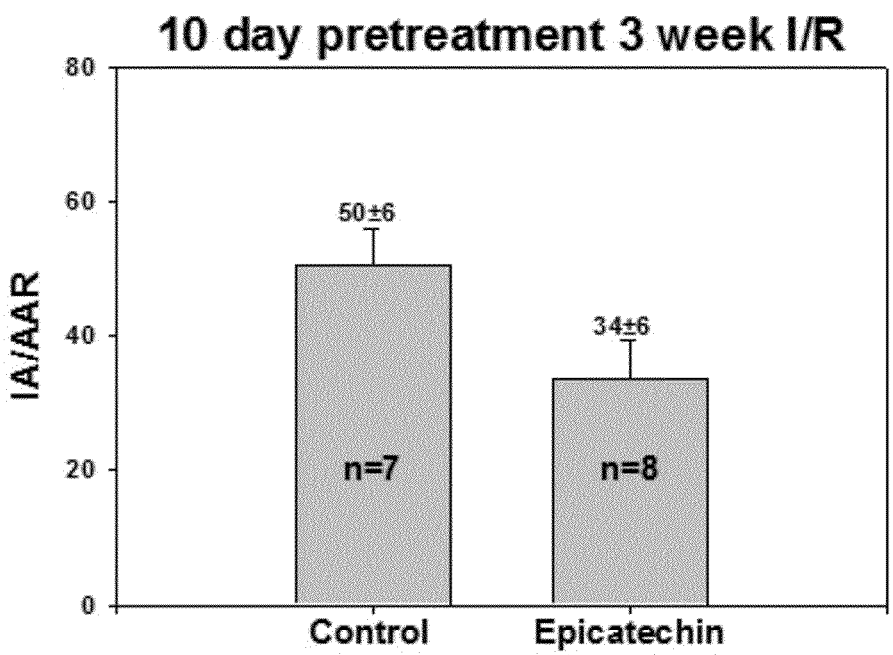
FIG. 6 is a bar graph of average and mean±SEM values recorded for infarct area (infarct area/area at risk: IA/AAR) in control and epicatechin treated animals 3 weeks after IR.
Figure 7:
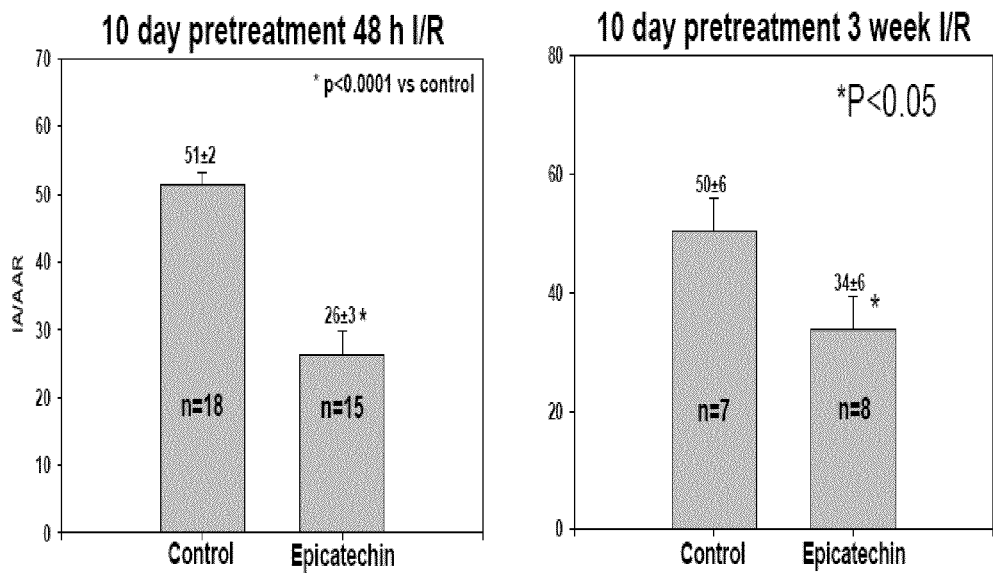
FIG. 7 are bar graphs of average and mean±SEM values recorded for infarct size in control and epicatechin treated animals 48 h and 3 weeks after IR. As can be observed early (48 h) cardioprotection generated by epicatechin is sustained 3 weeks after IR injury.

Infarct size and morphometry: FIG. 7 summarizes results observed at 48 h of IR and 3 week results. For the 10 day pre-treatment groups (FIG. 2A), infarct area was 51.4±1.8% vs. 26.3±3.4% with epicatechin (P<0.0001). Area at risk values for 10 day animals were similar between groups (FIG. 1).

In the 3 week analysis, IR animals infarct area was 50.4±5.6% vs. 33.7±5.5% with epicatechin (p=0.05). As shown in Table 1B, IR animals treated with epicatechin demonstrate comparable morphometric changes to those of 3 week untreated animals. Anterior wall vs. septal wall thicknesses yielded a statistical difference only in the vehicle treated IR group where the infarcted (anterior) wall became thinner. Changes in infarct size and morphometry appear independent from altered hemodynamics since epicatechin did not modify these in a manner that would explain the results.

The data demonstrate that epicatechin has the capacity to act as a short and long-term cardioprotectant in the setting of IR injury.

Ten day epicatechin results yielded a significant reduction in MI size at 48 h. The 48 h time point was selected to be able to clearly distinguish regions of necrotic tissue from viable myocardium. A means by which epicatechin decreases MI size can include reductions in afterload (lowering of blood pressure). Ten days of treatment in noninfarcted animals did not reduce blood pressure and thus, changes in afterload fail to explain the observed effects.

The purpose behind the study of 3 weeks post-IR animals was to determine the extent to which there was a sustained reduction in tissue injury with treatment. Results yield a reduction in scar size of ~33%. Ventricular morphometry results, one way to assess both favorable and adverse cardiac remodeling, did not show adverse effects of epicatechin. In fact, these results show that the ventricular wall characteristics are similar to that of animals with no infarction, revealing that epicatechin has favorable effects on cardiac remodeling.

Without being bound by theory, it is possible that the mechanisms of action of epicatechin cardioprotection are related to reduced levels of tissue oxidative stress and protease activity in injured regions of myocardium or induction of stem cell migration to areas of damaged tissues or epicatechin may provide a favorable medium for stem cell proliferation.

Example 2

Adult male Sprague-Dawley rats (Harlan, Indianapolis, Ind.) weighing ~250 g were used. Epicatechin (1 mg/kg/day; Sigma-Aldrich, St. Louis, Mo.) or vehicle (water) was administered orally by gavage once/day beginning 10 days before thoracotomy and continuing until the time of the terminal study (48 h or 3 weeks). Thoracotomy was performed at day 10. In the sham group, the chest was only opened and closed; no artery was permanently occluded. For the infarct group, the left anterior descending coronary artery was permanently occluded. In the 48 hour treatment arm, the animals were allowed to heal with treatment of epicatechin at 1 mg/kg/day continued for 48 hours. At 48 hours the animals were anesthetized and hemodynamics recorded. The heart was excised and for infarcted animals only the infarct size and heart structure (morphometry) were determined. In the 3 week treatment arm, the animals were allowed to heal for 3 weeks with daily treatment of epicatechin at 1 mg/kg/day. At 3 weeks the animals were anesthetized and hemodynamics recorded. The heart was excised and for infarcted animals only the infarct size and heart structure (morphometry) were determined.

Methods of determining infarct size, hemodynamics, tissue collection statistical analysis is as described in Example 1.

Figure 8:
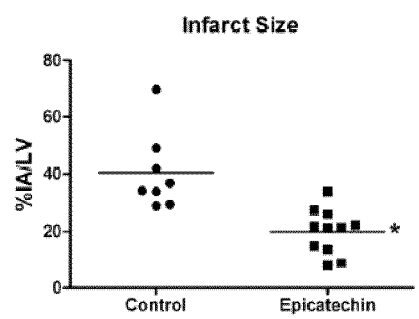
FIG. 8 is a bar graph of infarct size recorded in control and epicatechin treated animals 48 h after permanent coronary occlusion. A highly significant difference in infarct size is seen 48 h after coronary occlusion in treated animals.
Figure 8:
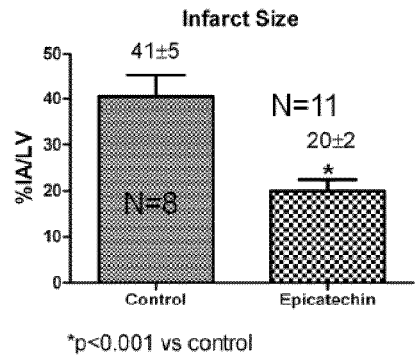

At 48 h after coronary occlusion epicatechin reduces infarct size by 50% (FIG. 8). This effect cannot be explained by the current understanding of the pathophysiology of cardiac injury in the setting of a complete interruption of blood flow.

Figure 9A:
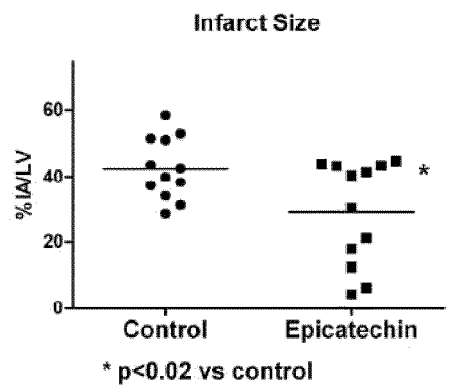
FIG. 9A-B are graphs depicting infarct size lesions. (a) Bar graph of the infarct size recorded in control and epicatechin treated animals 3 weeks after coronary occlusion. A non-significant trend (P=0.09) towards reductions in infarct size is seen 3 weeks after coronary occlusion in treated animals. (B) Bar graph of the wall thicknesses of the infarct region and septal wall. As can be observed the use of epicatechin led to a significant preservation of wall thickness in the infarct region implying anti-remodeling effects of the compound.
Figure 9A:
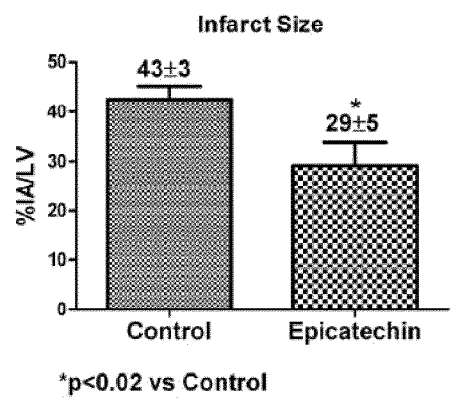
Figure 9B:
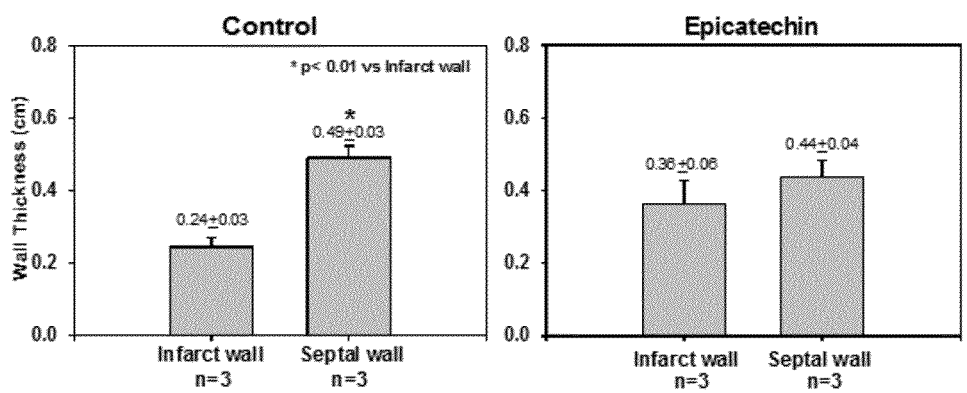

At 3 weeks after infarction epicatechin significantly reduced infarct size by 33% (FIG. 9a). These data are accompanied by the preservation of infarcted wall (anterior wall/AW) thickness (FIG. 9b). Thinning of the myocardial wall was seen in control animals with permanent occlusion but not in animals treated with epicatechin, suggesting that epicatechin prevents adverse ventricular remodeling after myocardial infarction. These data suggest that continued treatment with epicatechin preserves tissue viability and acts as an anti-remodeling agent. These results again, cannot be explained on the basis of alterations in hemodynamic parameters. Epicatechin treatment in sham (non-infarcted) or infarcted animals does not modify baseline hemodynamics and thus its capacity to reduce blood pressure cannot account for the observed cardioprotective effects (Tables 2, 4). As shown in Table 2, results from the analysis of hemodynamic values recorded 48 post-surgery indicate no adverse effects of epicatechin treatment on hemodynamic parameters in sham animals. As shown in Table 2, the use of epicatechin in infarcted animals did not yield alterations in hemodynamic parameters that would explain changes observed in infarct size (see FIG. 8). As shown in Table 4, results from the analysis of hemodynamic values recorded 3 weeks post-surgery indicate no adverse effects of epicatechin treatment on these parameters. As shown in Table 4, the use of epicatechin in infarcted animals did not yield alterations in hemodynamic parameters that would either represent adverse effects or explain the changes observed in infarct (scar) size and wall thickness (i.e.

chamber remodeling) observed at 3 weeks (see FIG. 9). Epicatechin treatment of infarcted animals does not adversely affect cardiac structure as assessed from results derived from morphometric measurements (Tables 3, 5). As shown in Table 4, results from the analysis of infarct (anterior wall or AW) and septal wall thicknesses indicate no significant differences amongst the groups studied. As shown in Table 3, 5, results from the analysis of cardiac morphometry indicate no significant differences amongst the groups studied. As shown in Table 5, results from the analysis of cardiac morphometry indicate no significant differences amongst the groups studied. Thus, the use of epicatechin does not alter normal cardiac structure but in fact helps maintain normal cardiac structure in the setting of permanent artery occlusion (FIG. 9B).

TABLE 2

Hemodynamic parameters recorded in sham rats and infarcted rats 48 h after thoracotomy.
Hemodynamic data 48 h Permanent Coronary Occlusion

|  | Sham | Sham + Epicatechin | PCO | PCO + epicatechin |
| --- | --- | --- | --- | --- |
| Group Size | 5 | 4 | 6 | 11 |
| HR (bpm) | 319 ± 12 | 334 ± 10 | 333 ± 17 | 342 ± 8 |
| LVPSP (mmHg) | 100 ± 2 | 102 ± 2 | 98.4 ± 4 | 107 ± 4 |
| LVEDP (mmHg) | 6.8 ± 0.9 | 4.3 ± 1.2 | 8.2 ± 4.2 | 5.8 ± 1.2 |
| MAP (mmHg) | 83 ± 3 | 83 ± 2 | 76 ± 6 | 91 ± 5 |

Animals were either treated with vehicle only (water) or treated with epicatechin (1 mg/kg/day) for 10 days prior to surgery and until the time of sacrifice. Values are mean ± SEM
HR = heart rate, LVPSP = left ventricular peak systolic pressure, LVEDP = left ventricular end diastolic pressure, MAP = mean arterial pressure

TABLE 3

Cardiac morphometry recorded in sham infarcted rats 48 h after thoracotomy.
Cardiac Morphometry data for 48 h Permanent Coronary Occlusion
MORPHOMETRY

|  | Sham | Sham + epicatechin | PCO | PCO + epicatechin |
| --- | --- | --- | --- | --- |
| Group Size | 5 | 5 | 8 | 11 |
| AW thickness (mm) | 0.51 ± 0.08 | 0.54 ± 0.05 | 0.47 ± 0.06 | 0.57 ± 0.03 |
| SW thickness (mm) | 0.39 ± 0.04 | 0.33 ± 0.06 | 0.55 ± 0.02 | 0.57 ± 0.02 |

Animals were treated as above. Wall thicknesses are in milimeters. Values are mean ± SEM.
Morphometry data obtained from either sham or 3 week PCO Epicatechin groups were pretreated for 10 d. Values shown are mean ± S.E.M.
*p < 0.01 vs. sham;
+p < 0.01 vs. IR SW thickness.
AW, anterior wall; SW, septal wall.

TABLE 4

Hemodynamic parameters recorded in sham and infarcted rats 3 weeks after thoracotomy.
Hemodynamic data 3 week Permanent Coronary Occlusion

|  | Sham | Sham + Epicatechin | PCO | PCO + epicatechin |
| --- | --- | --- | --- | --- |
| Group Size | 11 | 8 | 12 | 14 |
| HR (bpm) | 294 ± 11 | 303 ± 10 | 273 ± 9 | 268 ± 10 |
| LVPSP (mmHg) | 112 ± 6 | 118 ± 4 | 104 ± 2 | 102 ± 3* |
| LVEDP (mmHg) | 7.4 ± 0.4 | 6.4 ± 0.9 | 14 ± 2*+ | 11 ± 1 |
| MAP (mmHg) | 85 ± 6 | 92 ± 4 | 83 ± 4 | 82 ± 2 |

Animals were either treated with vehicle only (water) or treated with epicatechin (1 mg/kg/day) for 10 days prior to surgery and until the time of sacrifice. HR = heart rate (bpm), EDP = end-diastolic pressure, SBP = systolic pressure, MAP = mean aortic pressure. Pressures are in mmHg. Values are mean ± SEM.
*P < 0.05.
HR = heart rate, LVPSP = left ventricular peak systolic pressure, LVEDP = left ventricular end diastolic pressure, MAP = mean arterial pressure;
*p < 0.05 vs Sham + Epicatechin,
+p < 0.05 vs Sham Control

TABLE 5

Cardiac morphometry recorded in sham rats and infarcted rats 3 weeks after thoracotomy.
Morphometry data for 3 week PCO
MORPHOMETRY

|  | Sham | Sham + epicatechin | PCO | PCO + epicatechin |
| --- | --- | --- | --- | --- |
| Group Size | 11 | 9 | 12 | 12 |
| HW/BW | 3.70 ± 0.2 | 3.82 ± 0.3 | 5.0 ± 1.2* | 4.4 ± 0.7 |
| Outer LV diam. (mm) | 1.466 ± 0.061 | 1.469 ± 0.075 | 1.500 ± 0.032 | 1.495 ± 0.031 |
| Inner LV diam. (mm) | 0.513 ± 0.023 | 0.490 ± 0.046 | 0.645 ± 0.03* | 0.546 ± 0.046 |
| AW thickness (mm) | 0.61 ± 0.03 | 0.58 ± 0.05 | 0.32 ± 0.03+ | 0.446 ± 0.04 |
| SW thickness (mm) | 0.38 ± 0.04 | 0.38 ± 0.04 | 0.492 ± 0.01 | 0.475 ± 0.02 |

Animals were treated as above. Outer and inner diameters are in milimeters. Values are mean ± SEM.
Morphometry data obtained from either sham or 3 week PCO Epicatechin groups were pretreated for 10 d. Values shown are mean ± S.E.M.
*p < 0.01 vs. sham;
+p < 0.01 vs. PCO SW thickness.
HW/BW, heart weight-to-body weight ratio; LV, left ventricle; AW, anterior wall; SW, septal wall.

Epicatechin can be used as prophylactically or near the time of the temporary or permanent occlusion of an artery (similar to what occurs in a heart attack) for the reduction of organ (heart and other) infarct size.

In addition, for those patients suffering from a heart attack, epicatechin or its pharmaceutically acceptable salt can be administered (alone or in combination with doxycycline) after the heart attack to limit the development of adverse chamber remodeling thus, preventing the development of post-infarction heart failure.

Example 3

The purpose of this study is to examine the effects of epicatechin treatment on grafted stem cells used to repair the injured heart. The overall objective is to demonstrate that the use of epicatechin pre-treatment allows for improved engraftment, survival and differentiation of stem cells into the cardiac phenotype leading to improved contractile function and reduced levels of adverse remodeling. Stem cells are derived from embryonal, hematopoietic, mesenchymal, adipose or cardiac sources. Stem cells to be engrafted are marked using fluorescent tags to be able to visualize/track them after delivery into infarcted myocardium.

Study animals (e.g. rats) are pre-treated with either vehicle (water) or epicatechin (1 mg/kg/day) for 10 days prior to coronary occlusion via a thoracotomy. Ischemia-reperfusion injury is induced by occluding the coronary artery for 45 min and then releasing the occlusion as disclosed herein. Stem cell injection at the site of ischemia is made 10 min after reperfusion. Animals are allowed to recover under continuing treatment for varying periods of time (between 3-21 days). At pre-determined time points, e.g. 2 days, 10 days, 21 days, animals are anesthetized and cardiac structure/function evaluated using echocardiography. Hearts are then excised and the chamber morphometry measured. Stem cell survival and differentiation are characterized via fluorescent microscopy and immunostaining.

Example 4

It has been shown that administration of epicatechin after myocardial ischemia leads to favorable cardiac remodeling in the ventricle. This favorable cardiac remodeling can be applied to patients with atrial fibrillation/flutter that have adverse remodeling in the atrium.

300 patients with new onset atrial fibrillation are randomized into two groups (one given 1 mg/kg/day epicatechin and one given a placebo pill). Groups are matched for baseline demographic and disease characteristics (e.g. left atrial size, cardiovascular risk factors). Arrhythmia burden in the short term is assessed in these groups by giving patients a holter monitor after 10 days of treatment and assessing arrhythmia burden (amount of time a patient is in atrial fibrillation). These patients are also followed over the course of years (e.g. 5 years) to assess recurrence of atrial fibrillation. The patients obtain yearly cardiac echocardiograms to assess if there is an increase in left atrial size (e.g. one way to assess unfavorable remodeling).

Example 5

The major cause of death from subarachnoid hemorrhage is from cerebral vasospasm which is thought to be a very inflammatory reaction that is triggered by the blood leak from the ruptured aneurysm. There is also an ischemia-reperfusion injury that can occur.

200 patients with subarachnoid hemorrhage are randomized by Fisher score or Hunt-Hess grade to two groups. One group receives 1 mg/kg/day epicatechin and the other a placebo pill). The incidence of cerebral vasospasm, as assessed by transcranial Doppler and/or cerebral angiogram, and death are assessed between the two groups, during their hospitalization and up to 1 year after the subarachnoid hemorrhage.

In a related study, patients who develop cerebral vasospasm after subarachnoid hemorrhage are randomized to receive either administration generally at the time of cerebral angiogram of a single dose of epicatechin (between about 0.1 mg/kg and about 1 mg/kg) intra-arterially with intra-arterial calcium channel blockers (the current standard of care) during cerebral angiogram or to the control group receiving only intra-arterial calcium channel blocker. Any difference in long and short terms outcomes between the groups (such as cerebral infarction, death, functional status after discharge from hospitalization) are assessed during their hospitalization and up to 1 year after the subarachnoid hemorrhage.

Figure 10:
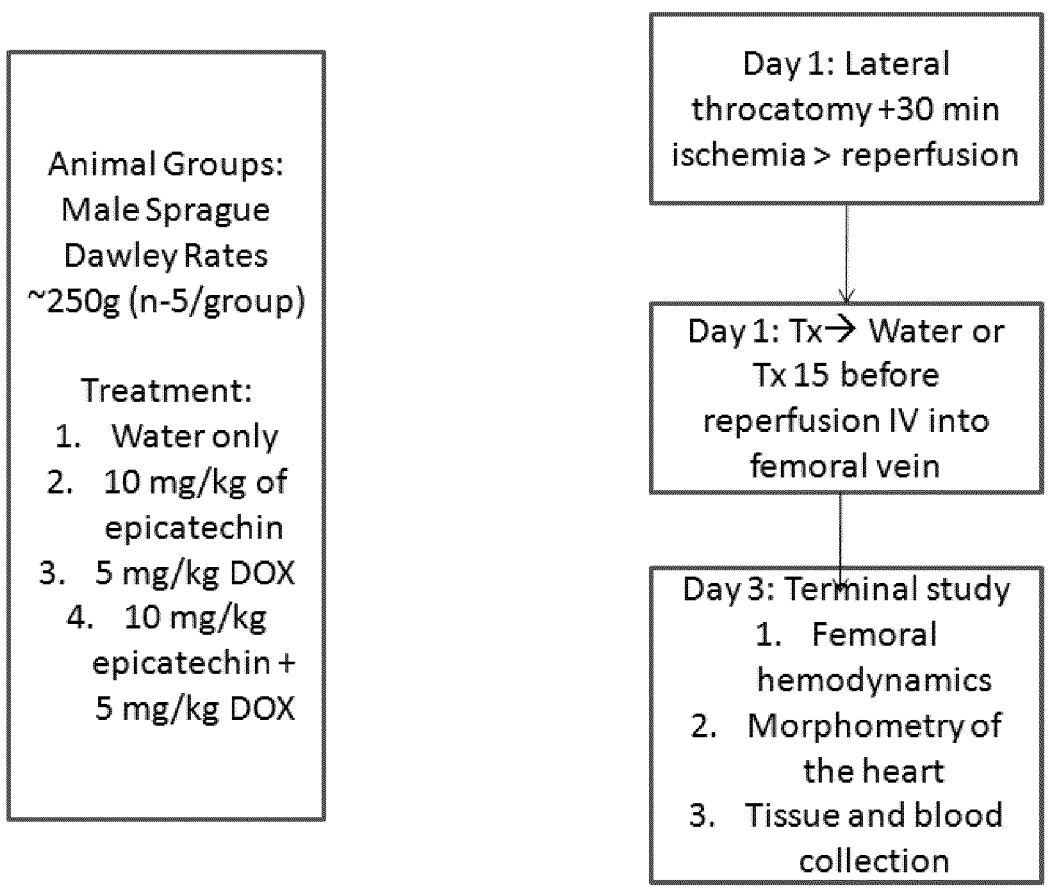
FIG. 10 shows a diagram of a study design of the disclosure.
Figure 11:
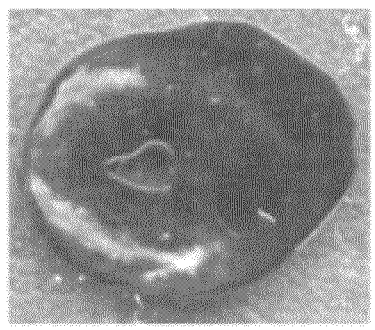
FIG. 11 shows section staining infarct size 48 hours after IR.
Figure 11:
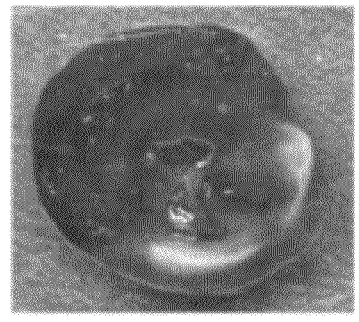
Figure 11:
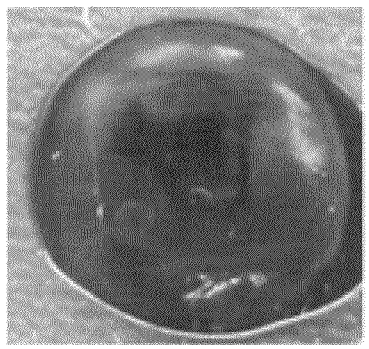
Figure 11:
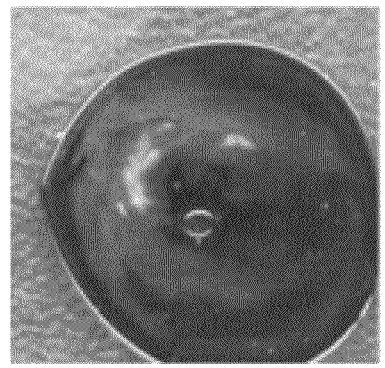
Figure 12:
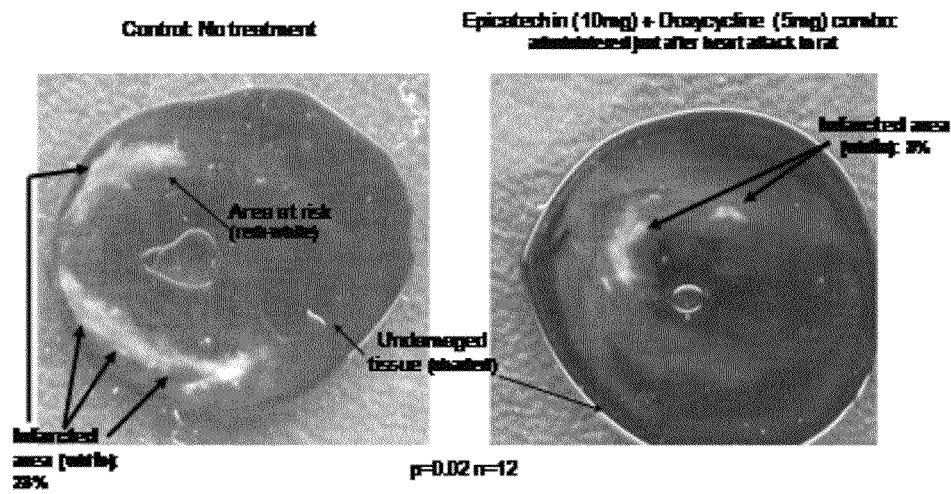
FIG. 12 shows section staining of epicatechin and DOX sections. The staining shows that combination therapy reduces heart tissue damage by about ~71%.
Figure 13:
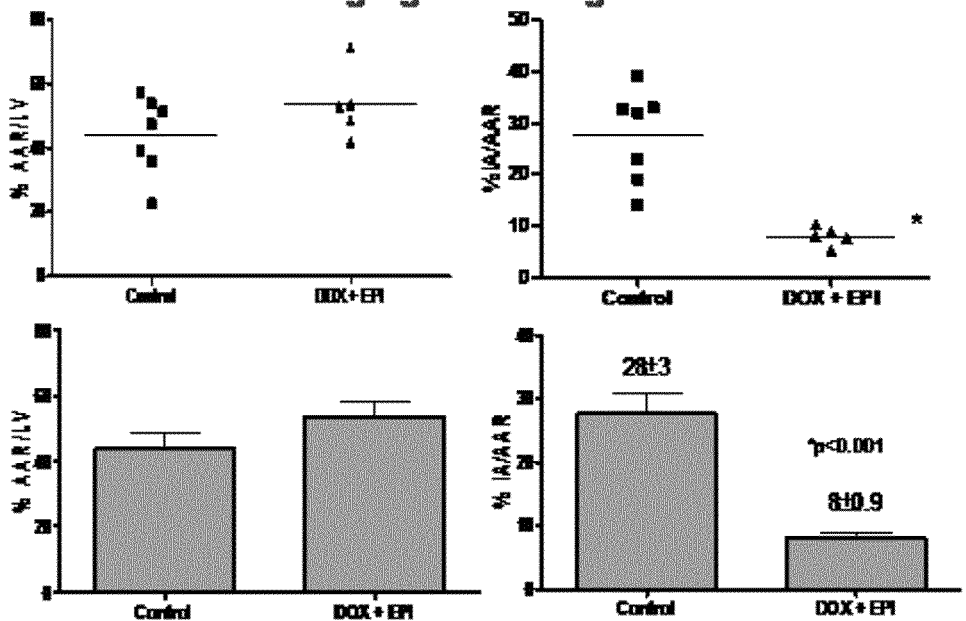
FIG. 13 are plots shows 48 hour infarct size in 10 mg/kg EPI+5 mg/kg DOX single IV.
Figure 14:
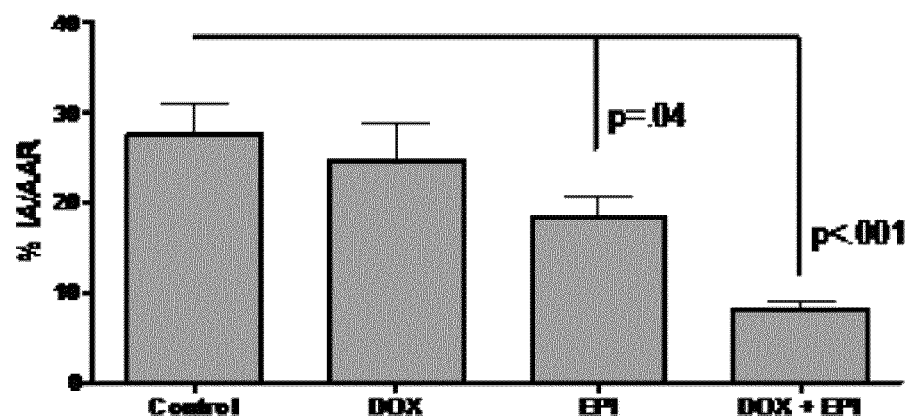
FIG. 14 shows all results of infarct size at 48 hours and single IV therapy.
Figure 15:
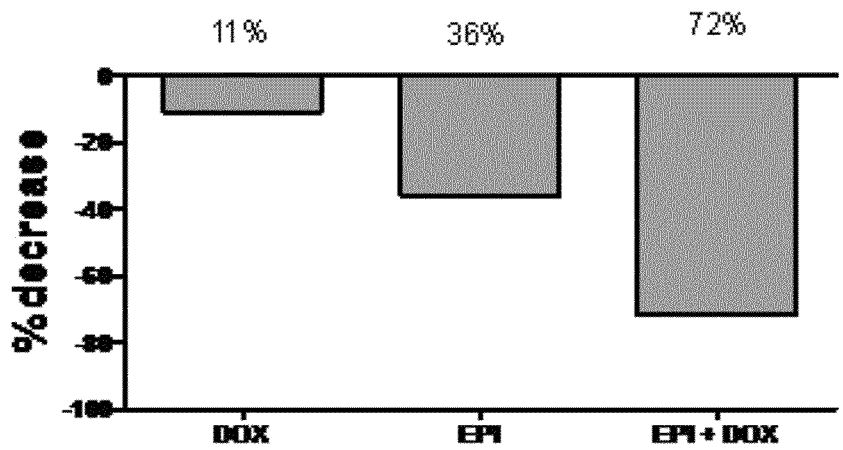
FIG. 15 is a plot showing that combined therapy can have synergistic effects.

FIG. 10 depicts a study design of the disclosure used to demonstrate the synergistic effects of an epicatechin (e.g., epigalocatechin) with a tetracycline (e.g., doxycyline). Male Sprague Dawley rats (~250 g) were divided into 4 groups (i) Water only, (ii) 10 mg/kg of epicatechin, (iii) 5 mg/kg DOX and (iv) 10 mg/kg epicatechin+5 mg/kg DOX (n=5/group). Lateral thoracotamy with 30 minutes ischemia>reperfusion was performed a treated per the groups above 15 min before reperfusion IV in the femoral artery. Animals were humanely sacrificed and the hearts were then section and stained to examine tissue injury.

FIG. 11-15 shows the effects of epicatechin, and epicatechin and DOX therapy. The data demonstrates that IV epicatechin (10 mg/kg) reduces IR induced infarct size at 48 h by 36%. IV DOX (5 mg/kg) reduces IR induced infact size at 4 hours by ~10%. Combined IV epicatechin+DOX reduces IR induced infarct size at 48 hours by ~72%. The effects are independent of changes in afterload (hemodynamics). There were no apparent adverse effects. Combination therapy thus limits damage to muscle and extracellular matrix compartments ultimately reducing MI size and adverse chamber remodeling.

Figure 17:
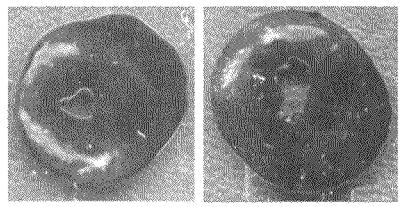
FIG. 17 shows with the effect of increasing epicatechin dose on infarct size.
Figure 17:
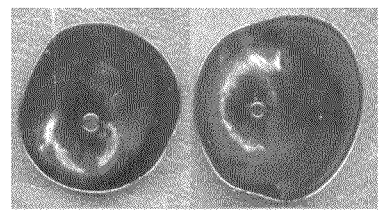
Figure 17:
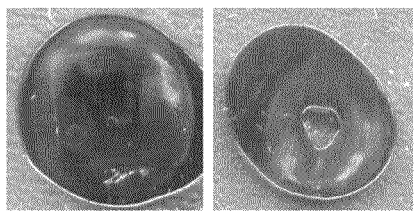
Figure 17:
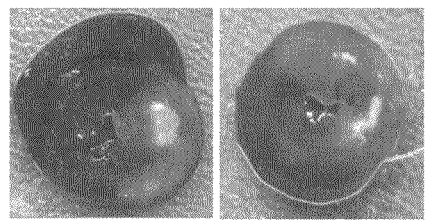
Figure 17:
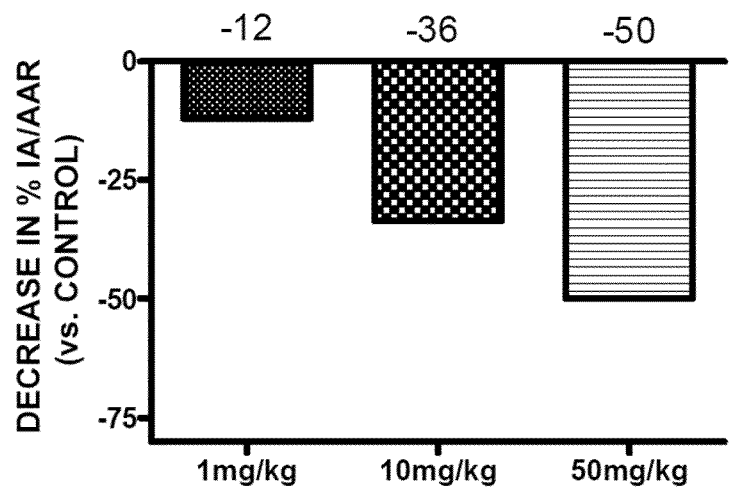
Figure 18:
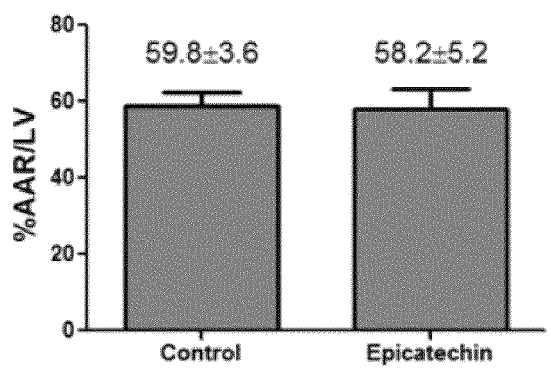
FIG. 18 shows the effect of epicatechin treatment on infarct size following an ischemia time of 45 minutes.
Figure 18:
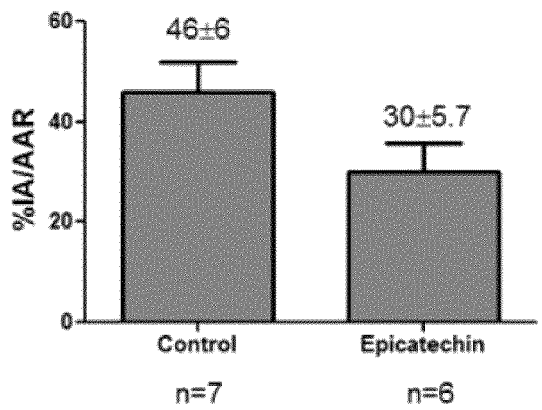

FIG. 17 shows a dose-response for the effect of epicatechin on infarct size. There was a decrease in ischemic area and area at risk at all doses tested, with an increasing effect seen with increasing dose. FIG. 18 shows that this effect persists even with extended infarction time. In this example, the total ischemia time was 45 minutes, with a single IV dose of 10 mg/kg given 15 minutes prior to reperfusion, followed by an oral maintenance dose of epicatechin at a concentration of 1 mg/kg/day for three weeks. At 3 weeks the animals were anesthetized and hemodynamics recorded. The heart was excised and the infarct size and heart structure (morphometry) were determined.

Figure 16:
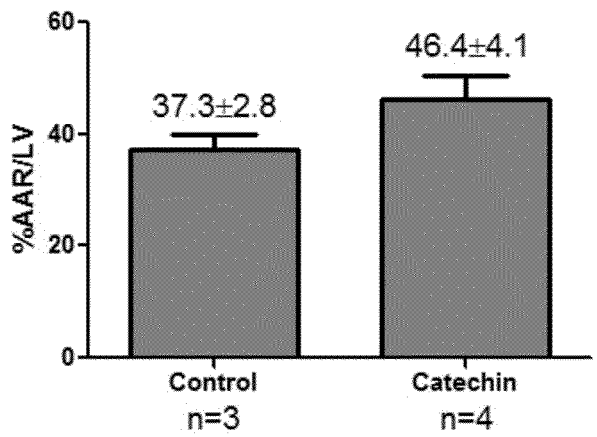
FIG. 16 shows the effect of catechin on areas at risk and infarction size.
Figure 16:
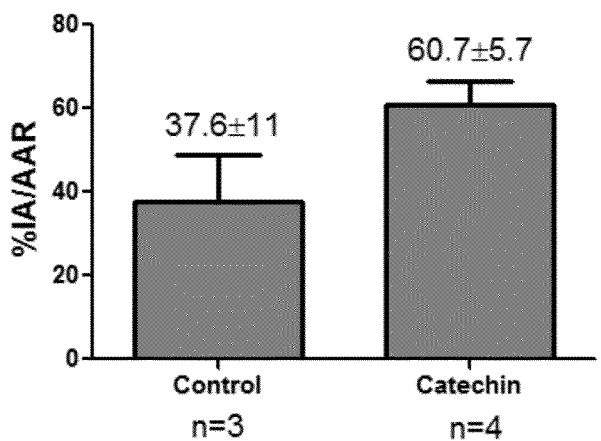

Catechin also exhibited no effect on area at risk or infarction size when administered to Male Sprague Dawley rats according to the methods described in Example 5 above. FIG. 16. This demonstrates that the stereochemical difference in epicatechin (3R(−)) relative to the closely related catechin (3S(+)) is critical to the protective effect seen in these studies.

Example 6

Adult male Sprague-Dawley rats (Harlan, Indianapolis, Ind.) weighing 250-300 g were used. Animals were anesthetized by intraperitoneal injection of ketamine (100 mg/kg) and xylazine (10 mg/kg), intubated, and positive-pressure ventilated. A left thoracotomy was then performed.

In animals undergoing the ischemia reperfusion protocol, the left anterior descending coronary artery was ligated for 45 minutes, released and the suture left in place as a point of reference. The chest was closed in layers and animals allowed to recover. Successful occlusion and reperfusion was verified by visual inspection of left ventricle (LV) color. Epicatechin (10 mg/kg; Sigma-Aldrich, St. Louis, Mo.), doxycycline (2.5 mg/kg or 5 mg/kg; Sigma-Aldrich, St. Louis, Mo.), minocycline (1 mg/kg or 5 mg/kg; Sigma-Aldrich, St. Louis, Mo.), or a combination was administered intravenously 15 minutes prior reperfusion. Controls received water.

Figure 19:
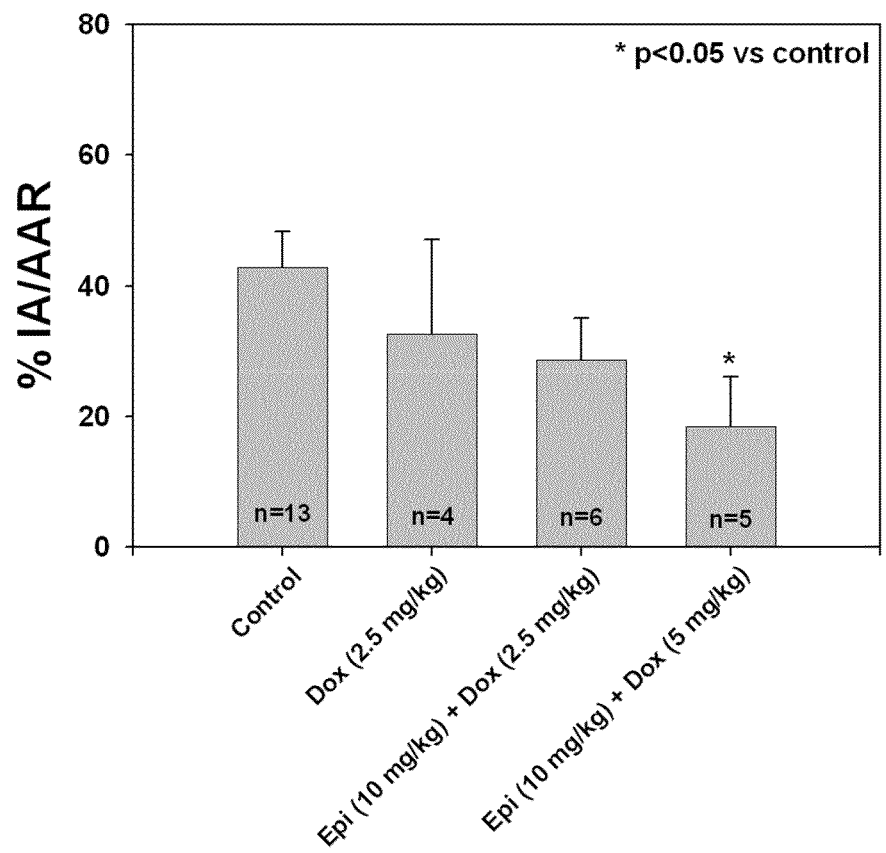
FIG. 19 shows dose effects of doxycycline.
Figure 20:
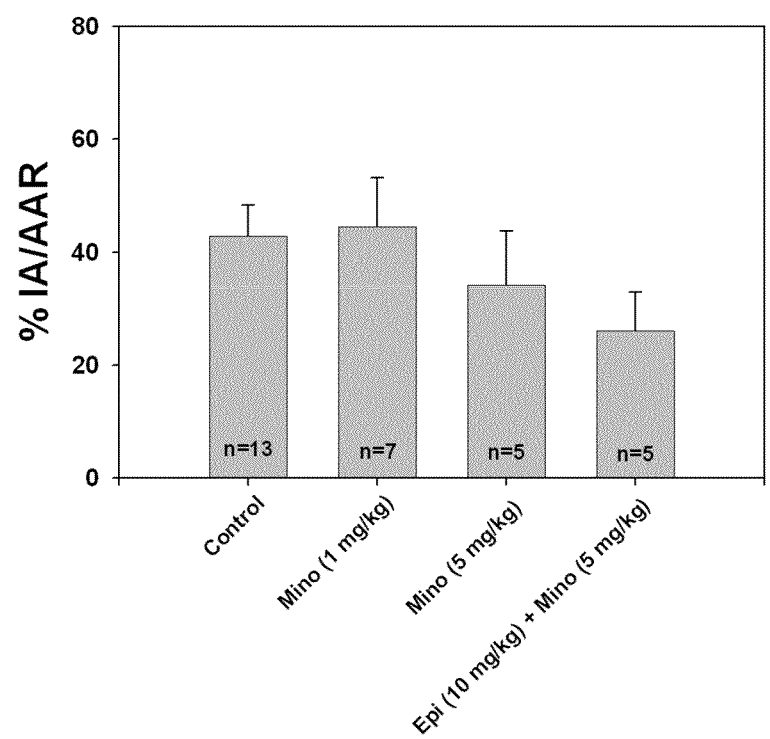
FIG. 20 shows that with minocycline and epicatechin administration there is a trend toward decreased infarct size.

Epicatechin treatment (1 mg/kg/day) only was continued via oral gavage until the time of sacrifice. Animals were sacrificed 48 h post IR, hearts excised and weighed. The area at risk (AAR) was determined by the reocclusion of the snare and infusion of trypan blue into the cannulated aorta. Hearts was sectioned into five 2 mm rings and stained using triphenyltetrazolium chloride. Computer assisted image analysis was used using blinded operators. Results are expressed as infarct area (IA) as a function of the area at risk (AAR) (see, e.g., FIGS. 19 and 20).

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of treating or inhibiting ischemic/reperfusion injury comprising: contacting a subject with an epicatechin or a pharmaceutically acceptable salt and doxycycline in an amount sufficient to reduce cell and/or tissue damage.

2. The method of claim 1, wherein the tetracycline or the tetracycline derivative inhibits matrix metalloproteinase activity.

3. The method of claim 2, wherein the matrix metalloproteinase activity comprises MMP-9 activity.

4. The method of claim 1, further comprising administering a reperfusion/thrombolytic agent.

5. The method of claim 3, further comprising administering an NMDA receptor antagonist.

6. A method of treating organ or tissue ischemia in a subject in need thereof, comprising:
    administering to said subject an effective amount of one or more drugs selected from the group consisting of epicatechin, derivatives thereof and pharmaceutically acceptable salts thereof, together with doxycycline.

7. A method according to claim 6, wherein said organ or tissue ischemia event is an acute ischemic or ischemia/reperfusion (IR) event.

8. A method according to claim 6, wherein said organ or tissue ischemia event is caused by a condition selected from the group consisting of myocardial infarction, renal injury, total coronary occlusion, myocardial ischemia, stroke, aortic aneurysm, atrial fibrillation, and medical intervention causing temporary acute ischemia.

9. A method according to claim 8, wherein said organ or tissue ischemia event is caused by coronary artery bypass graft ("CABG") surgery, aneurysm repair, angioplasty, or administering a radiocontrast agent.

10. A method according to claim 6, wherein epicatechin, a derivative, or a pharmaceutically acceptable salt thereof is administered together with doxycycline by a parenteral route.

11. A method according to claim 10, wherein said parenteral route is an intravenous route.

12. A method according to claim 10, wherein said subject is further administered (i) epicatechin, a derivative, or a pharmaceutically acceptable salt thereof, doxycycline, or both (i) and (ii) by parenteral route.

13. A method according to claim 6, wherein said administering step is performed within 48 hours of the onset of said organ or tissue ischemia in the subject, within 48 hours of initiating a medical procedure presenting a risk of organ or tissue ischemia on the subject, or within 48 hours of presentation of the subject for medical evaluation of possible organ or tissue ischemia.

* * * * *